US008494784B2

(12) United States Patent
Huynh et al.

(10) Patent No.: US 8,494,784 B2
(45) Date of Patent: Jul. 23, 2013

(54) SYSTEM AND METHOD FOR IDENTIFICATION OF MICRORNA TARGET SITES AND CORRESPONDING TARGETING MICRORNA SEQUENCES

(75) Inventors: Tien Huynh, Yorktown Heights, NY (US); Kevin Charles Miranda, McDowall (AU); Isidore Rigoutsos, Astoria, NY (US)

(73) Assignee: International Business Machines Corporation, Armonk, NY (US)

( * ) Notice: Subject to any disclaimer, the term of this patent is extended or adjusted under 35 U.S.C. 154(b) by 809 days.

(21) Appl. No.: 12/135,551

(22) Filed: Jun. 9, 2008

(65) Prior Publication Data
US 2009/0012720 A1    Jan. 8, 2009

Related U.S. Application Data

(63) Continuation of application No. 11/351,821, filed on Feb. 10, 2006, now abandoned.

(60) Provisional application No. 60/652,499, filed on Feb. 11, 2005.

(51) Int. Cl.
*G06F 19/24* (2011.01)
*G06F 19/22* (2006.01)

(52) U.S. Cl.
CPC ..................................... *G06F 19/22* (2013.01)
USPC .......................................................... 702/20

(58) Field of Classification Search
None
See application file for complete search history.

(56) References Cited

U.S. PATENT DOCUMENTS
6,108,666 A    8/2000 Floratos et al.

OTHER PUBLICATIONS

Hofacker, I. L. Nucl. Acids Res. 31(13), 3429-3431 Jul. 2003.*
Lewis, B. P., Shih, I.-H., Jones-Rhoades, M. W., Bartel, D. P., and Burge, C. B. Cell 115(7), 787-798 Dec. 2003.*
Lim, L. P., Lau, N. C., Weinstein, E. G., Abdelhakim, A., Yekta, S., Rhoades, M. W., Burge, C. B., and Bartel, D. P. Genes & Development 17(8), 991-1008 Apr. 2003.*
Rajewsky, N. and Socci, N. D. Developmental Biology 267(2), 529-535 Mar. 2004.*

(Continued)

*Primary Examiner* — Lori A. Clow
*Assistant Examiner* — Soren Harward
(74) *Attorney, Agent, or Firm* — Ryan, Mason & Lewis, LLP

(57) ABSTRACT

A method for determining whether a nucleotide sequence contains a microRNA binding site and which microRNA will bind thereto is provided. For example, in one aspect of the invention, a method for determining whether a nucleotide sequence contains a microRNA binding site and which microRNA sequence will bind thereto is comprised of the following steps. One or more patterns are generated by processing a collection of known mature microRNA sequences. The reverse complement of each generated patter is then computed. One or more attributes are then assigned to the reverse complement of the one or more generated patterns. The one or more patterns that correspond to a reverse complement having one or more assigned attributes that satisfy at least one criterion are thereafter subselected. Each subselected pattern is then used to analyze the nucleotide sequence, such that a determination is made whether the nucleotide sequence contains a microRNA binding site and which microRNA sequence will bind thereto.

33 Claims, 9 Drawing Sheets

OTHER PUBLICATIONS

Rhoades, M. W., Reinhart, B. J., Lim, L. P., Burge, C. B., Bartel, B., and Bartel, D. P. Cell 110(4), 513-520 Aug. 2002.*

Rigoutsos, I. And Floratos, A. Bioinformatics 14(1), 55-67 Feb. 1998.*

Shibuya, T. And Rigoutsos, I. Nucl. Acids Res. 30(12), 2710-2725 Jun. 2002.*

Wang, X. J., Reyes, J., Chua, N. H. & Gaasterland, T. Prediction and identification of *Arabidopsis thaliana* micrornas and their mrna targets. Genome Biology 5, R65.1-R65.15 (2004).*

I.L. Hofacker et al., "Fast Folding and Comparison of RNA Secondary Structures," Monatshefte für Chemie (Chemical Monthly), vol. 125, pp. 167-188, 1994.

D.H. Mathews et al., "Expanded Sequence Dependence of Thermodynamic Parameters Improves Prediction of RNA Secondary Structure," J. Mol. Biol., vol. 288, pp. 911-940, 1999.

S. Griffiths-Jones et al., "Rfam: An RNA Family Database," Nucleic Acids Research, vol. 31, No. 1, pp. 439-441, 2003.

S.F. Altschul et al., "Basic Local Alignment Search Tool," J Mol Biol., vol. 215, pp. 403-410, 1990.

I. Rigoutsos et al., "Combinatorial Pattern Discovery in Biological Sequences: The TEIRESIAS Algorithm," Bioinformatics, vol. 14, No. 1, pp. 55-67, 1998.

A. Stabenau et al., "The Ensembl Core Software Libraries," Genome Research, vol. 14, pp. 929-933, 2004.

A. Stark et al., "Identification of Drosophila MicroRNA Targets," PLoS Biology, vol. 1, Issue 3, pp. 397-409, 2003.

M. Rehmsmeier et al., "Fast and Effective Prediction of MicroRNA/Target Duplexes," RNA, vol. 10, pp. 1507-1517, 2004.

A.J. Enright et al., "MicroRNA Targets in Drosophila," Genome Biology, vol. 5, Issue 1, Article R1, pp. 1-14, 2003.

U.S. Appl. No. 11/352,152, filed Feb. 10, 2006, I. Rigoutsos et al.

U.S. Appl. No. 11/351,951, filed Feb. 10, 2006, T. Huynh et al.

E.C. Lai et al., "Computational Identification of Drosophila MicroRNA Genes," Genome Biology, vol. 4, Issue 7, Article R42, pp. 1-20, 2003.

L.P. Lim et al., "The MicroRNAs of *Caenorhabditis elegans*," Genes and Development, vol. 17, pp. 991-1008, 2003.

E. Berezikov et al., "Phylogenetic Shadowing and Computational Identification of Human MicroRNA Genes," Cell, vol. 120, pp. 21-24, 2005.

L.P. Lim et al., "Vertebrate MicroRNA Genes," Science Magazine, vol. 299, p. 1540, Mar. 2003.

I. Bentwich et al., "Identification of Hundreds of Conserved and Nonconserved Human microRNAs," Nature Genetics, vol. 37, No. 7, pp. 766-770, Jul. 2005.

J.C. Wootton et al., "Statistics of Local Complexity in Amino Acid Sequences and Sequence Databases," Computers and Chemistry, vol. 17, No. 2, pp. 149-163, 1993.

Brazma et al., Approaches to the Automatic Discovery of Patterns in Biosequences, Journal of Computational Biology 5, 279-305 (1998).

Cowan, Expected Frequencies of DNA Patterns using Whittle's Formula, Journal of Applied Probability 28, 886-892 (1991).

* cited by examiner

FIG. 3A

| GENE | POSITION OF REPORTED SITE FROM TO | MicroRNA BINDING SITE DETECTED AS FUNCTION OF PATTERN THRESHOLD 20 25 30 35 40 45 50 55 60 65 70 | NUMBER OF IDENTIFIED "TARGET ISLANDS" AS FUNCTION OF PATTERN THRESHOLD 20 25 30 35 40 45 50 55 60 65 70 |
|---|---|---|---|
| CAENORHABDITIS ELEGANS | | | |
| lin28 | 328 342 | | 8 8 7 6 6 6 5 5 4 3 3 |
| lin41 | 689 710 | | 12 12 12 13 10 8 8 7 7 7 4 |
| lin41 | 738 757 | | 12 12 12 13 10 8 8 7 7 7 4 |
| cog-1 | 257 285 | | 7 6 5 5 5 3 2 2 2 2 1 |
| DROSOPHILA MELANOGASTER | | | |
| hid | 874 896 | | 31 31 25 29 23 21 21 19 19 18 17 |
| hid | 1711 1731 | | 31 31 25 29 23 21 21 19 19 18 17 |
| hairy | 441 465 | | 9 9 7 6 8 7 7 6 5 5 5 |
| grim | 63 86 | | 15 11 12 12 11 11 11 10 10 9 8 |
| sickle | 34 58 | | 13 14 12 11 11 11 11 10 9 9 7 |
| bagpipe | 86 109 | | 2 1 1 1 1 1 1 1 1 1 1 |
| HOMO SAPIENS | | | |
| hoxb8 | 411 432 | | 9 10 10 10 9 7 7 4 4 4 4 |
| mtpn | 3126 3141 | | 35 41 32 31 27 24 19 16 15 14 13 |
| lin28 | 890 913 | | 31 28 29 25 24 21 19 16 16 12 11 |
| mapk14. | 652 669 | | 26 28 26 26 24 22 21 17 17 17 15 |
| fbxwib | 2393 2415 | | 31 33 30 28 22 22 21 17 15 13 12 |
| laminin | 210 223 | | 16 15 14 15 15 15 11 10 8 6 5 |
| dmtf1 | 130 146 | | 12 14 14 13 11 10 10 9 7 6 5 |
| clock | 215 233 | | 34 32 31 32 31 29 27 23 22 20 18 |
| cgi38 | 295 311 | | 4 4 3 2 2 2 2 2 2 2 1 |
| smc1 | 74 91 | | 62 65 59 63 57 56 51 46 42 36 35 |
| brn3b | 464 470 | | 17 19 19 17 14 11 9 9 8 7 6 |
| brn3b | 103 109 | | 17 19 19 17 14 11 9 9 8 7 6 |
| enx1 | 115 121 | | 3 3 2 2 2 2 2 2 2 2 2 |
| enx1 | 60 66 | | 3 3 2 2 2 2 2 2 2 2 2 |
| bdnf | 221 227 | | 30 34 34 29 27 24 22 20 18 16 13 |
| bdnf | 1323 1329 | | 30 34 34 29 27 24 22 20 18 16 13 |
| g6pd | 434 440 | | 6 6 4 4 4 3 1 0 0 0 0 |
| g6pd | 98 104 | | 6 6 4 4 4 3 1 0 0 0 0 |
| smad | 104 110 | | 2 2 1 1 1 0 0 0 0 0 0 |
| smad | 47 53 | | 2 2 1 1 1 0 0 0 0 0 0 |
| nmyc | 495 501 | | 12 10 11 9 9 9 8 6 6 5 4 |
| pten | NA NA | | |
| pten | NA NA | | |
| sdf1 | NA NA | | |
| sdf1 | NA NA | | |
| notch2 | NA NA | | |
| mcsf1 | NA NA | | |
| mcsf1 | NA NA | | |
| delta | NA NA | | |
| delta | NA NA | | |

FIG. 3B

| miRNA | IDENTIFY REPORTED microRNA? ABOVE OUR STRINGENT THRESHOLDS? | ENERGY (DG) | SEQUENCE ID | PUBLICATION |
|---|---|---|---|---|
| CAENORHABDITIS ELEGANS | | | | |
| lin-4 | N/A | | F02E9.2a | Moss et al |
| let-7 | | -34.0 | C12C8.3a | Reinhart et al |
| let-7 | | -32.3 | C12C8.3a | Reinhart et al |
| lsy-6 | | -17.8 | R03C1.3a | Johnston & Horbert |
| DROSOPHILA MELANOGASTER | | | | |
| bantam | | -29.5 | CG5123-RA | Brennecke et al |
| bantam | | -37.2 | CG5123-RA | Brennecke et al |
| mir-7 | | -31.1 | CG6494-RA | Stark et al |
| mir-2b | | -30.0 | CG4345-RA | Stark et al |
| mir-2b | N/A | | CG13701-RA | Stark et al |
| mir-4 | N/A | – | CG7902-RA | Brennecke et al |
| HOMO SAPIENS | | | | |
| mir-196a | | -45.4 | ENST00000239144 | Yekta et al |
| mir-375 | | -23.4 | ENST00000222605 | Poy et al |
| let-7b | | -35.9 | ENST00000254231 | Kiriakidou et al |
| mir-24 | | -37.4 | ENST00000229794 | Kiriakidou et al |
| mir-103 | N/A | | ENST00000265094 | Kiriakidou et al |
| mir-199b | | -29.7 | ENST00000264144 | Kiriakidou et al |
| mir-15a | | -30.9 | ENST00000331242 | Kiriakidou et al |
| mir-141 | | -24.4 | ENST00000309964 | Kiriakidou et al |
| mir-16 | N/A N/A | | ENST00000314601 | Kiriakidou et al |
| let-7e | N/A N/A | | ENST00000322213 | Kiriakidou et al |
| mir-23a | N/A N/A | | ENST00000281321 | Lewis et al |
| mir-23a | N/A N/A | | ENST00000281321 | Lewis et al |
| mir-101 | N/A N/A | | ENST00000320356 | Lewis et al |
| mir-101 | N/A N/A | | ENST00000320356 | Lewis et al |
| mir-1b | N/A N/A | | ENST00000314915 | Lewis et al |
| mir-1b | N/A N/A | | ENST00000314915 | Lewis et al |
| mir-1b | N/A N/A | | ENST00000291567 | Lewis et al |
| mir-1b | N/A N/A | | ENST00000291567 | Lewis et al |
| mir-26a | N/A N/A | | ENST00000302085 | Lewis et al |
| mir-26a | N/A N/A | | ENST00000302085 | Lewis et al |
| mir-101 | N/A N/A | | ENST00000281043 | Lewis et al |
| mir-19a | – – | – | ENST00000307803 | Lewis et al |
| mir-19a | – – | – | ENST00000307803 | Lewis et al |
| mir-23a | – – | – | ENST00000343575 | Lewis et al |
| mir-23a | – – | – | ENST00000343575 | Lewis et al |
| mir-34 | – – | – | ENST00000277541 | Lewis et al |
| mir-130 | – – | – | ENST00000329608 | Lewis et al |
| mir-130 | – – | – | ENST00000329608 | Lewis et al |
| mir-34 | – – | – | – | Lewis et al |
| mir-34 | – – | – | – | Lewis et al |

FIG. 5A

| GENOME | NUMBER OF KNOWN MATURE microRNAs RFAM JUNE 2005 | NUMBER OF TRANSCRIPTS WITH A KNOWN 3'UTR SEQUENCE | NUMBER OF PREDICTED "TARGET ISLANDS" IN KNOWN 3'UTR SEQUENCES | NUMBER OF 3'UTR SEQUENCES CONTAINING ONE OR MORE "TARGET ISLANDS" (% OF TOTAL UTRs) | NUMBER OF NTS COMPRISING ALL KNOWN 3'UTR SEQUENCES | NUMBER OF NTS COMPRISING PREDICTED 3'UTR "TARGET ISLANDS" (% OF TOTAL NTS) | NUMBER OF TRANSCRIPTS WHOSE 3'UTRs PARTICIPATE IN RNA/RNA COMPLEXES WITH KNOWN microRNAs FROM THE CORRESPONDING GENOME (% OF TOTAL TRANSCRIPTS) |
|---|---|---|---|---|---|---|---|
| C. ELEGANS | 115 | 13,186 | 27,700 | 9,752 (73.9%) | 3,048,704 | 1,259,056 (41.3%) | 4,132 (31.4%) |
| D. MELANOGASTER | 78 | 14,965 | 63,918 | 13,104 (87.6%) | 6,671,035 | 2,984,758 (44.7%) | 5,475 (36.6%) |
| M. MUSCULUS | 233 | 20,257 | 180,157 | 18,597 (91.8%) | 18,058,224 | 8,680,125 (48.0%) | 16,324 (80.6%) |
| H. SAPIENS | 313 | 25,589 | 243,211 | 23,616 (92.3%) | 25,597,040 | 11,624,638 (45.4%) | 21,330 (83.3%) |

FIG. 5B

| GENOME | NUMBER OF KNOWN MATURE microRNAs RFAM JUNE 2005 | NUMBER OF TRANSCRIPTS WITH A KNOWN 5'UTR SEQUENCE | NUMBER OF PREDICTED "TARGET ISLANDS" IN KNOWN 5'UTR SEQUENCES | NUMBER OF 5'UTR SEQUENCES CONTAINING ONE OR MORE "TARGET ISLANDS" (% OF TOTAL UTRs) | NUMBER OF NTS COMPRISING ALL KNOWN 5'UTR SEQUENCES | NUMBER OF NTS COMPRISING PREDICTED 5'UTR "TARGET ISLANDS" (% OF TOTAL NTS) | NUMBER OF TRANSCRIPTS WHOSE 5'UTRs PARTICIPATE IN RNA/RNA COMPLEXES WITH KNOWN microRNAs FROM THE CORRESPONDING GENOME (% OF TOTAL TRANSCRIPTS) |
|---|---|---|---|---|---|---|---|
| C. ELEGANS | 115 | 11,713 | 7,085 | 3,654 (31.2%) | 797,941 | 318,329 (39.9%) | 1,208 (10.3%) |
| D. MELANOGASTER | 78 | 15,461 | 37,078 | 12,139 (32.7%) | 4,129,409 | 958,931 (23.2%) | 4,639 (30.0%) |
| M. MUSCULUS | 233 | 19,978 | 31,967 | 10,298 (51.5%) | 4,398,970 | 1,456,850 (33.1%) | 7,222 (36.1%) |
| H. SAPIENS | 313 | 25,042 | 46,007 | 13,350 (53.3%) | 6,947,437 | 2,091,398 (30.1%) | 10,130 (40.4%) |

FIG. 6A

| GENOME | AVERAGE NUMBER OF 3'UTRs PREDICTED TO BE THE TARGET OF A KNOWN microRNA FROM THE CORRESPONDING GENOME | AVERAGE NUMBER OF KNOWN microRNAs PREDICTED TO TARGET A SINGLE 3'UTR FROM THE CORRESPONDING GENOME |
|---|---|---|
| C. ELEGANS | 73 | 2 |
| D. MELANOGASTER | 149 | 2 |
| M. MUSCULUS | 817 | 12 |
| H. SAPIENS | 1008 | 15 |

FIG. 6B

| GENOME | AVERAGE NUMBER OF 5'UTRs PREDICTED TO BE THE TARGET OF A KNOWN microRNA FROM THE CORRESPONDING GENOME | AVERAGE NUMBER OF KNOWN microRNAs PREDICTED TO TARGET A SINGLE 5'UTR FROM THE CORRESPONDING GENOME |
|---|---|---|
| C. ELEGANS | 21 | 2 |
| D. MELANOGASTER | 119 | 2 |
| M. MUSCULUS | 148 | 5 |
| H. SAPIENS | 201 | 6 |

FIG. 7

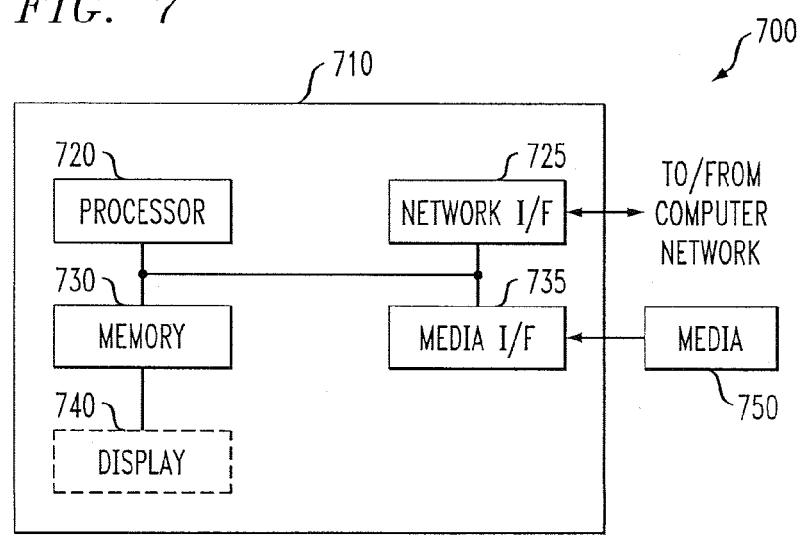

SEQUENCE LISTING

<160> NUMBER OF SEQ ID NOS: 11

<210> SEQ ID NO 1
<211> LENGTH: 16
<212> TYPE: PRT
<213> ORGANISM: Unknown
<220> FEATURE:
<223> OTHER INFORMATION: The pattern is an example from the domain of
      amino acid sequences and describes the calcium binding motif of
      cadherin proteins.
<220> FEATURE:
<221> NAME/KEY: MISC_FEATURE
<222> LOCATION: (4)..(4)
<223> OTHER INFORMATION: X is defined as any amino acid.
<220> FEATURE:
<221> NAME/KEY: MISC_FEATURE
<222> LOCATION: (8)..(8)
<223> OTHER INFORMATION: X is defined as any amino acid.
<220> FEATURE:
<221> NAME/KEY: MISC_FEATURE
<222> LOCATION: (10)..(10)
<223> OTHER INFORMATION: X is defined as any amino acid.
<220> FEATURE:
<221> NAME/KEY: MISC_FEATURE
<222> LOCATION: (15)..(15)
<223> OTHER INFORMATION: X is defined as any amino acid.

<400> SEQUENCE: 1

Leu Ile Val Xaa Leu Ile Val Xaa Asp Xaa Asn Asp Asn His Xaa Pro
1               5                   10                  15

<210> SEQ ID NO 2
<211> LENGTH: 28
<212> TYPE: DNA
<213> ORGANISM: Unknown
<220> FEATURE:
<223> OTHER INFORMATION: The pattern is a typical mature microRNA
      pattern used for clarification purposes.
<220> FEATURE:
<221> NAME/KEY: misc_feature
<222> LOCATION: (5)..(5)
<223> OTHER INFORMATION: n is defined as a wild card, and can represent
      any of the four nucleotides.
<220> FEATURE:
<221> NAME/KEY: misc_feature
<222> LOCATION: (14)..(14)
<223> OTHER INFORMATION: n is defined as a wild card, and can represent
      any of the four nucleotides.
<220> FEATURE:
<221> NAME/KEY: misc_feature
<222> LOCATION: (15)..(15)
<223> OTHER INFORMATION: n is defined as a wild card, and can represent
      any of the four nucleotides.
<220> FEATURE:
<221> NAME/KEY: misc_feature
<222> LOCATION: (25)..(25)
<223> OTHER INFORMATION: n is defined as a wild card, and can represent
      any of the four nucleotides.

<400> SEQUENCE: 2
atcgnttttt cggnnatata tgcgnctt                                              28

<210> SEQ ID NO 3
<211> LENGTH: 28
<212> TYPE: DNA
<213> ORGANISM: Unknown
<220> FEATURE:
<223> OTHER INFORMATION: The pattern is the reverse complement of the
      typical microRNA pattern used for clarification purposes.

-continued

```
<220> FEATURE:
<221> NAME/KEY: misc_feature
<222> LOCATION: (4)..(4)
<223> OTHER INFORMATION: n is defined as a wild card, and can represent
      any of the four nucleotides.
<220> FEATURE:
<221> NAME/KEY: misc_feature
<222> LOCATION: (14)..(14)
<223> OTHER INFORMATION: n is defined as a wild card, and can represent
      any of the four nucleotides.
<220> FEATURE:
<221> NAME/KEY: misc_feature
<222> LOCATION: (15)..(15)
<223> OTHER INFORMATION: n is defined as a wild card, and can represent
      any of the four nucleotides.
<220> FEATURE:
<221> NAME/KEY: misc_feature
<222> LOCATION: (28)..(28)
<223> OTHER INFORMATION: n is defined as a wild card, and can represent
      any of the four nucleotides.

<400> SEQUENCE: 3
aagncgcata tatnnccgaa aaacgatn                                            28

<210> SEQ ID NO 4
<211> LENGTH: 23
<212> TYPE: DNA
<213> ORGANISM: Unknown
<220> FEATURE:
<223> OTHER INFORMATION: The pattern is a trinucleotide form being
      computed for frequency in a source.
<220> FEATURE:
<221> NAME/KEY: misc_feature
<222> LOCATION: (3)..(22)
<223> OTHER INFORMATION: n is defined as a wild card, and can be
      represented by any of the four nucleotides.

<400> SEQUENCE: 4
aannnnnnnn nnnnnnnnnn nna                                                 23

<210> SEQ ID NO 5
<211> LENGTH: 23
<212> TYPE: DNA
<213> ORGANISM: Unknown
<220> FEATURE:
<223> OTHER INFORMATION: The pattern is a trinucleotide form being
      computed for frequency in a source.
<220> FEATURE:
<221> NAME/KEY: misc_feature
<222> LOCATION: (2)..(21)
<223> OTHER INFORMATION: n is defined as a wild card, and can be
      represented by any of the four nucleotides.

<400> SEQUENCE: 5
tnnnnnnnnn nnnnnnnnnn ntt                                                 23

<210> SEQ ID NO 6
<211> LENGTH: 14
<212> TYPE: DNA
<213> ORGANISM: Unknown
<220> FEATURE:
<223> OTHER INFORMATION: The pattern is a trinucleotide form being used
      to estimate the probability that a given pattern could be
      generated from a random database.
<220> FEATURE:
<221> NAME/KEY: misc_feature
<222> LOCATION: (2)..(3)
<223> OTHER INFORMATION: n is defined as a wild card, and can be
      represented by any of the four nucleotides.
<220> FEATURE:
<221> NAME/KEY: misc_feature
<222> LOCATION: (6)..(6)
<223> OTHER INFORMATION: n is defined as a wild card, and can be
      represented by any of the four nucleotides.
```

```
<220> FEATURE:
<221> NAME/KEY: misc_feature
<222> LOCATION: (8)..(9)
<223> OTHER INFORMATION: n is defined as a wild card, and can be
      represented by any of the four nucleotides.
<220> FEATURE:
<221> NAME/KEY: misc_feature
<222> LOCATION: (11)..(13)
<223> OTHER INFORMATION: n is defined as a wild card, and can be
      represented by any of the four nucleotides.

<400> SEQUENCE: 6
annatncnnt nnng                                                         14

<210> SEQ ID NO 7
<211> LENGTH: 14
<212> TYPE: DNA
<213> ORGANISM: Unknown
<220> FEATURE:
<223> OTHER INFORMATION: The pattern is a trinucleotide form being used
      to estimate the probability that a given pattern could be
      generated from a random database.
<220> FEATURE:
<221> NAME/KEY: misc_feature
<222> LOCATION: (2)..(3)
<223> OTHER INFORMATION: n is defined as a wild card, and can be
      represented by any of the four nucleotides.
<220> FEATURE:
<221> NAME/KEY: misc_feature
<222> LOCATION: (6)..(6)
<223> OTHER INFORMATION: n is defined as a wild card, and can be
      represented by any of the four nucleotides.
<220> FEATURE:
<221> NAME/KEY: misc_feature
<222> LOCATION: (8)..(9)
<223> OTHER INFORMATION: n is defined as a wild card, and can be
      represented by any of the four nucleotides.
<220> FEATURE:
<221> NAME/KEY: misc_feature
<222> LOCATION: (11)..(13)
<223> OTHER INFORMATION: n is defined as a wild card, and can be
      represented by any of the four nucleotides.

<400> SEQUENCE: 7
annatncnnt nnng                                                         14

<210> SEQ ID NO 8
<211> LENGTH: 28
<212> TYPE: DNA
<213> ORGANISM: Unknown
<220> FEATURE:
<223> OTHER INFORMATION: The pattern is a typical mature microRNA
      pattern used for clarification purposes.
<220> FEATURE:
<221> NAME/KEY: misc_feature
<222> LOCATION: (5)..(5)
<223> OTHER INFORMATION: n is defined as a wild card, and can be
      represented by any of the four nucleotides.
<220> FEATURE:
<221> NAME/KEY: misc_feature
<222> LOCATION: (14)..(15)
<223> OTHER INFORMATION: n is defined as a wild card, and can be
      represented by any of the four nucleotides.
<220> FEATURE:
<221> NAME/KEY: misc_feature
<222> LOCATION: (25)..(25)
<223> OTHER INFORMATION: n is defined as a wild card, and can be
      represented by any of the four nucleotides.

<400> SEQUENCE: 8
atcgnttttt cggnnatata tgcgnctt                                          28
```

-continued

```
<210> SEQ ID NO 9
<211> LENGTH: 28
<212> TYPE: DNA
<213> ORGANISM: Unknown
<220> FEATURE:
<223> OTHER INFORMATION: The pattern is the reverse complement of the
      typical mature microRNA pattern used for clarification purposes.
<220> FEATURE:
<221> NAME/KEY: misc_feature
<222> LOCATION: (4)..(4)
<223> OTHER INFORMATION: n is defined as a wild card, and can be
      represented by any of the four nucleotides.
<220> FEATURE:
<221> NAME/KEY: misc_feature
<222> LOCATION: (14)..(15)
<223> OTHER INFORMATION: n is defined as a wild card, and can be
      represented by any of the four nucleotides.
<220> FEATURE:
<221> NAME/KEY: misc_feature
<222> LOCATION: (28)..(28)
<223> OTHER INFORMATION: n is defined as a wild card, and can be
      represented by any of the four nucleotides.

<400> SEQUENCE: 9
aagncgcata tatnnccgaa aaacgatn                                          28

<210> SEQ ID NO 10
<211> LENGTH: 10
<212> TYPE: DNA
<213> ORGANISM: Unknown
<220> FEATURE:
<223> OTHER INFORMATION: The pattern is a fixed sequence used in the
      analysis to pair each microRNA with every one of the target
      islands at all possible offsets.

<400> SEQUENCE: 10
gcggggacgc                                                              10

<210> SEQ ID NO 11
<211> LENGTH: 22
<212> TYPE: RNA
<213> ORGANISM: Artificial
<220> FEATURE:
<223> OTHER INFORMATION: The pattern is a randomly shuffled version of
      the microRNA 134 used in the analysis.

<400> SEQUENCE: 11
agacuagcgg uaucuuuauc cc                                                22
```

SYSTEM AND METHOD FOR IDENTIFICATION OF MICRORNA TARGET SITES AND CORRESPONDING TARGETING MICRORNA SEQUENCES

CROSS REFERENCE TO RELATED APPLICATIONS

This application is a continuation of pending U.S. application Ser. No. 11/351,821 filed on Feb. 10, 2006, the disclosure of which is incorporated herein by reference. U.S. application Ser. No. 11/351,821 claims the benefit of U.S. Provisional Application No. 60/652,499 filed Feb. 11, 2005, the disclosure of which is incorporated by reference herein.

U.S. application Ser. No. 11/351,821 is related to U.S. application Ser. No. 11/351,951 filed on Feb. 10, 2006, the disclosure of which is incorporated by reference herein. Also, U.S. application Ser. No. 11/351,821 is related to U.S. application Ser. No. 11/352,152 filed on Feb. 10, 2006, the disclosure of which is incorporated by reference herein.

FIELD OF THE INVENTION

The present invention relates to genes and, more particularly, to ribonucleic acid interference molecules and their role in gene expression.

BACKGROUND OF THE INVENTION

The ability of an organism to regulate the expression of its genes is of central importance to life. A breakdown in this homeostasis leads to disease states, such as cancer, where a cell multiplies uncontrollably, to the detriment of the organism. The general mechanisms utilized by organisms to maintain this gene expression homeostasis are the focus of intense scientific study.

It recently has been discovered that some cells are able to down-regulate their gene expression through certain ribonucleic acid (RNA) molecules. Namely, when RNA molecules are in contact with certain of the cells' protein machinery they act as potent gene translation inhibitors, also referred to as post-transcriptional gene silencing mechanisms. This process, which is known as RNA interference, or RNAi, has been found to function both in mediating resistance to endogenous and exogenous pathogenic nucleic acids, as well as, in regulating the expression of genes inside cells.

The term 'gene expression,' as used herein, refers generally to the transcription of messenger-RNA (mRNA) from a gene, and, e.g., its subsequent translation into a functional protein. One class of RNA molecules involved in gene expression regulation comprises microRNAs, which are endogenously encoded and regulate gene expression by either disrupting the translation process or by degrading mRNA transcripts, e.g., inducing post-transcriptional repression of one or more target sequences. Currently, hundreds of microRNAs exist for many genomes. However, only a handful of targets have been identified for only a small number of microRNAs.

The RNAi/post-transcriptional gene silencing mechanism allows an organism to employ short RNA sequences to either degrade or disrupt translation of mRNA transcripts containing a complementary or near-complementary sequence. Early studies suggested only a limited role for RNAi, that of a defense mechanism against foreign born pathogens. However, the subsequent discovery of many endogenously-encoded microRNAs pointed towards the possibility of this being a more general, in nature, control mechanism. Recent evidence has led the community to hypothesize that a wider spectrum of biological processes are affected by RNAi, thus extending the range of this presumed control layer. Despite being the focus of intense research investment, the manner in which a particular microRNA determines its specific gene target and exerts its control over the latter remains largely an open question. The magnitude of this problem has led experimentalists to rely increasingly upon computational methods as a source of guidance.

To date, the published computational methods for microRNA target site detection have been varied. One group of approaches employs modified versions of the dynamic programming solution to the local suffix alignment problem. A second group of methods is "signature-based" with the signature derived from the first 6-8 consecutive nucleotides in the 5' region ("seed region") of the microRNA. The methods employ this 'signature' explicitly as well as implicitly. Other schemes use hidden Markov models to find seed matches or are based on exhaustive schemes that calculate interactions for every offset of the target sequence of the microRNA and sub-select those of the relative placements which are deemed significant according to a specific statistical measure. Despite their methodological variety and the fact that the underlying computational methods can be applied to genomes in isolation, the majority of these approaches use the conservation of a potential binding site at orthologous positions across multiple species as a filtering criterion before they report any results.

In recent years, predictions made by many of these methods have been validated by experiments. Nonetheless, the number of confirmed microRNA/mRNA complexes remains very small by comparison. This underscores the inherent difficulty of the task and the need for continuing research in computational approaches that can address the problem at hand.

A better understanding of the mechanism of the RNA interference process would benefit the fight against disease, drug design and host defense mechanisms.

SUMMARY OF THE INVENTION

A method for determining whether a nucleotide sequence contains a microRNA binding site and which microRNA will bind thereto is provided. For example, in one aspect of the invention, a method for determining whether a nucleotide sequence contains a microRNA binding site and which microRNA sequence will bind thereto is comprised of the following steps. One or more patterns are generated by processing a collection of known mature microRNA sequences. The reverse complement of each generated pattern is then computed. One or more attributes are then assigned to the reverse complement of the one or more generated patterns. The one or more patterns that correspond to a reverse complement having one or more assigned attributes that satisfy at least one criterion are thereafter subselected. Each subselected pattern is then used to analyze the nucleotide sequence, such that a determination is made whether the nucleotide sequence contains a microRNA binding site and which microRNA sequence will bind thereto.

A more complete understanding of the present invention, as well as further features and advantages of the present invention, will be obtained by reference to the following detailed description.

BRIEF DESCRIPTION OF THE DRAWINGS

FIG. 3 is a table summarizing the performance of the inventive approach on experimentally validated microRNA binding sites;

FIG. 5A is a table summarizing the results of the microRNA target site predictions for the genomes of C. elegans, D. melanogaster, M. musculus and H. sapiens from the analysis of 3'UTRs;

FIG. 5B is a table summarizing the results of the microRNA target site predictions for the genomes of C. elegans, D. melanogaster, M. musculus and H. sapiens from the analysis of 5'UTRs;

FIG. 6A is a table summarizing the average number of transcripts that a known microRNA is predicted to target and the average number of known microRNAs that are predicted to hit a transcript, assuming that the targeting takes place through the 3'UTR of the transcripts;

FIG. 6B is a table summarizing the average number of transcripts that a known microRNA is predicted to target and the average number of known microRNAs that are predicted to hit a transcript assuming that the targeting takes place through the 5'UTR of the transcripts; and FIG. 7 is a block diagram of a system for determining whether a nucleotide sequence contains a microRNA binding site and which microRNA will bind thereto, in accordance with one embodiment of the present invention.

DETAILED DESCRIPTION OF PREFERRED EMBODIMENTS

Figure 1:
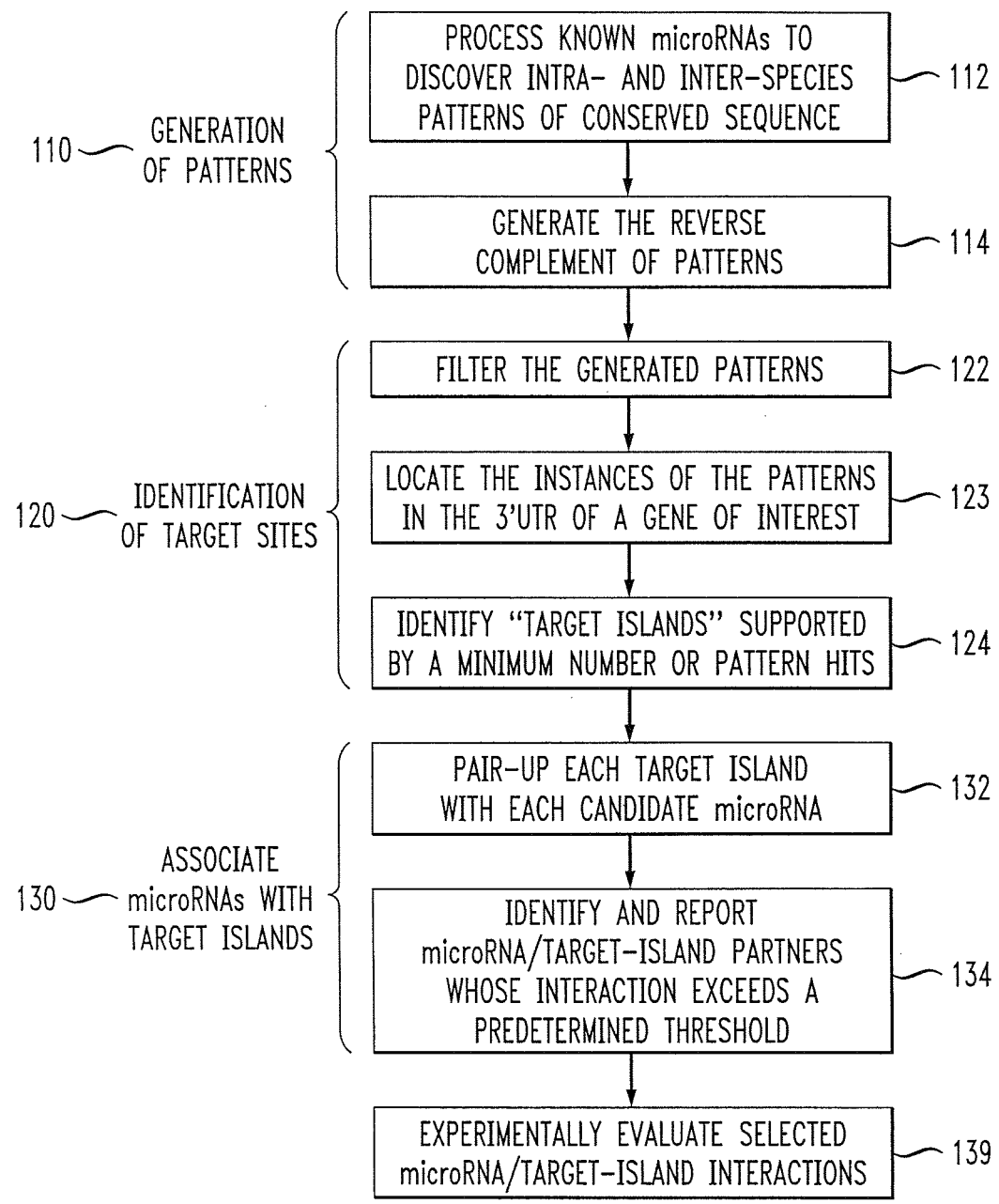
FIG. 1 is a flow diagram illustrating a method for identifying microRNA binding sites and corresponding microRNA sequences, according to one embodiment of the invention.

The teachings of the present invention relate to ribonucleic acid (RNA) molecules and their role in gene expression regulation. As mentioned above, a novel, pattern-based computational method for the identification of microRNA targets is provided. The method obviates the need for cross-species conservation, is applicable to any microRNA-containing genome and can identify target sites without knowing the targeting microRNA. The method can be, as an example only, applied to the genomes of C. elegans, D. melanogaster, M. musculus and H. sapiens. By way of example, such sequences are described in detail in Application No. 60/652,499, the disclosure of which is incorporated by reference herein. Also, such sequences are described in detail in the above-mentioned related U.S. patent application 11/352,152, the disclosure of which is incorporated herein.

The sequences referred to herein may be found in electronic text format as the file "1500-667CON_SequenceListing_ST25_7-28-2008.txt," created on Jul. 28, 2008, having a size of 8 KB, the contents of which are incorporated by reference herein; the file was submitted via EFS-Web.

Using a data repository that predates the corresponding validations, the method correctly predicts almost all of the experimentally-confirmed microRNA/target-mRNA interactions in each of these four genomes. With the help of a luciferase-based assay, additional experimental support of the predictive ability of the inventive approach is provided by confirming 70 novel targets for microRNAs miR-375 and miR-296. Additionally, using protein-antibody assays, YY additional targets for the embryonic-stem-cell specific microRNA miR-134 were validated. Herein, the prediction is made that approximately 74%, 88%, 92% of the transcripts in C. elegans, D. melanogaster, M. musculus and H. sapiens, respectively, are under RNAi control. The inventive approach readily extends to the discovery of microRNA precursors directly from genomic sequence and the initial estimates indicate that the potential number of endogenously-encoded microRNA precursors may be significantly higher than previously reported. A method for identifying microRNA precursor sequences and corresponding mature microRNA sequences from genomic sequences is described in detail in the above-mentioned related U.S. patent application 11/351, 951, the disclosure of which is incorporated herein.

Advantageously, the inventive approach obviates the need of cross-species sequence conservation, and is thus readily applicable to any genomic sequence independent of whether it has orthologues in other species. Importantly, the inventive approach can identify microRNA target sites without having to know the identity of the targeting microRNA. The capabilities of the inventive approach are demonstrated by first showing that the inventive approach correctly identifies many of the experimentally-validated microRNA targets sites and associated microRNA/mRNA complexes. Also, additional support of the abilities of the inventive approach is provided by describing the experimental validation, through a luciferase-reporter assay, of a combined 79 predicted targets for the mouse microRNAs miR-375, miR-134 and miR-296. Many of the validated microRNA/target pairs could not be predicted by other popular prediction tools as leading candidate complexes. Additional support of the predictive ability of the inventive approach is presented below. Therein, we show for 4 of the predicted targets of the embryonic-stem-cell-related miR-134 that the corresponding protein product is decreased in the presence of this microRNA with no concomitant decrease in messenger RNA levels, thus, implying that, for the tested targets, this microRNA acts by inhibiting translation. Using shuffled instances of the complete 3'UTRs (untranslated regions) for the transcripts that contained the 79 targets that we validated, the exceptional resilience to noise of the inventive approach is demonstrated.

FIG. 1 is a flow diagram illustrating a method for identifying microRNA binding sites and corresponding microRNA sequences, according to one embodiment of the invention. Underlying the inventive approach is a pattern-based methodology which discovers variable-length sequence fragments ('patterns') that recur in an input database a user-specified, minimum number of times. The number of discovered patterns, the exact locations of the instances of each pattern, the actual extent of each pattern, and finally the number of instances that a pattern has in the input database are, of course, not known ahead of time. Computationally, the pattern discovery problem is a much 'harder' problem than database searching. Indeed, pattern discovery is an NP-hard problem whereas database searching can be solved in polynomial time.

We will first describe step 110, the generation of patterns. The generation of patterns (step 110) is comprised of steps 112 and 114, as shown in FIG. 1.

Step 112 is the step of processing known microRNA sequences to discover intra- and inter-species patterns of conserved sequence segments.

The recurrent instances of a given sequence segment can be represented with the help of regular expressions with differing degrees of descriptive power. The expressions used in the present invention are composed of literals (solid characters from the alphabet of permitted symbols), wildcards (each denoted by '.' and representing any character), and sets of equivalent literals (each set being a small number of symbols, anyone of which can occupy the corresponding position). The distance between two consecutive occupied positions is assumed to be unchanged across all instances of the pattern (i.e., 'rigid patterns'). The pattern [LIV].[LIV].D.ND[NH].P (SEQ ID NO: 1) is an example from the domain of amino acid sequences and describes the calcium binding motif of cadherin proteins. The motif in question comprises exactly one of the amino acids {leucine, isoleucine, valine}, followed by any amino acid, followed again by exactly one of the amino acids {leucine, isoleucine, valine}, followed by any amino acid, followed by the negatively charged aspartate, etc. Typically, the presence of a statistically significant pattern in an unannotated amino acid sequence is taken as a sufficient condition to suggest the presence of the feature captured by the pattern.

In the context of the work described herein, the symbol set that we used comprises the four nucleotides {A,C,G,T} found in a deoxyribonucleic acid (DNA) sequence. The input set which we processed in order to discover patterns is Release 3.0 of the RFAM database, from January 2004 (Griffiths-Jones, S. et al. Rfam: an RNA family database. *Nucleic Acids Res.*, 31 439-441 (2003)). For simplicity, we use the corresponding DNA sequence for our work instead of the RNA sequence of the transcript (i.e. all of the sequences contain thymine (T) instead of uracil (U)). The use of a more-than-18-month-old release of the database as the training set was intentional. We wanted to gauge the ability of the inventive approach to correctly predict the target sites and microRNA/mRNA complexes which were reported in the literature after January 2004. Using an old version of RFAM is not necessary for the described inventive approach to work. In fact, in subsequent incarnations of the inventive approach, we have used the version of RFAM that was the latest available.

Unlike previously published computational methods for microRNA target prediction, the present invention makes use of the sequence information from all the microRNAs which are contained in the RFAM release, and independent of the organism in which they originate. The release in question contains microRNA sequences from the human, mouse, rat, worm, fly and several plant genomes. The simultaneous processing of microRNA sequences from distinct organisms permits the discovery of conserved sequences both within and across species and makes the method suitable for the analysis of more than one organism. We downloaded 644 mature microRNAs from the RFAM, Release 3.0 (January, 2004).

We used a scheme based on BLASTN to remove duplicate and near-duplicate entries from the initial collection (Altschul, S. F. Gish, W. Miller, W. Myers, E. W. Lipman, D. J. Basic local alignment search tool. *J Mol Biol.* 215 403-410 (1990)). The final set comprised 354 sequences of mature microRNAs such that no two remaining sequences agreed on more than 90% of their positions. We next describe in detail the BLASTN-based cleanup scheme.

We assume that we are given N sequences of variable length and a user-defined threshold X for the permitted, maximum remaining pair-wise sequence similarity. The sequence-based clustering scheme that we employed is shown below. Upon termination, the set CLEAN contains sequences no pair of which agrees on more than X % of the positions in the shorter of the two sequences. For our analysis, we set X=90%.

```
sort the N sequences in order of decreasing length; let S_i denote the i-th
sequence of the sorted set (i=1, ..., N)
CLEANE ← S_1
for i = 2 through N do
    use S_i as query to run BLAST against the current contents of CLEAN
    if the top BLAST hit T agrees with S_i at more than X % of the
    S_i's position
    then
        make S_i a member of the cluster represented by T ;
        discard S_i ;
    else
        CLEAN ← CLEAN 4 { S_i };
```

This non-redundant input was processed using the Teiresias algorithm in order to discover intra- and inter-species patterns of sequence conservation (Rigoutsos, I. and Floratos, A. Combinatorial pattern discovery in biological sequences: The TEIRESIAS algorithm. *Bioinformatics* 14 55-67 (1998)). The combinatorial nature of the algorithm and the guaranteed discovery of all patterns contained in the processed input makes Teiresias a good choice for addressing this task. The nature of the patterns that can be discovered is controlled by three parameters: L, the minimum number of symbols participating in a pattern; W, the maximum permitted span of any L consecutive (not contiguous) symbols in a pattern; and K, the minimum number of instances required of a pattern before it can be reported. Statistical significance requirements were also enforced. The significance of each pattern was estimated with the help of a second-order Markov chain which was built from actual genomic data. Application of the significance filter substantially reduced the number of patterns that were used in the subsequent phases of the algorithm. Details on the Teiresias algorithm and its properties, the three parameters L/W/K, and how to estimate log-probabilities are given below.

The Teiresias algorithm requires that the three parameters L, W and K be set. The three parameters that control the discovery process were set to L=4, W=12 and K=2. 120,789, 247 variable length patterns were discovered in the processed input set, typically spanning fewer than 22 positions. These patterns were replaced by their reverse complements, and for each of the reverse complements we estimated the log-probability to be the result of a random event. Patterns with log-probability >−32.0 were removed resulting in a final set of 233,554 statistically-significant patterns. We next describe in detail how the parameters control the number and character of the discovered patterns.

The parameter L controls the minimum possible size of the discovered patterns. The parameter W satisfies the inequality $W \geq L$ and controls the 'degree of conservation' across the various instances of the reported patterns. Setting W to smaller (respectively larger) values permits fewer (respectively more) mismatches across the instances of each of the discovered patterns. Finally, the parameter K controls the minimum number of instances that a pattern must have before it can be reported.

For a given choice of L, W and K Teiresias guarantees that it will report all patterns that have K or more appearances in the processed input and are such that any L consecutive (but not necessarily contiguous) positions span at most W positions. It is important to stress that even though no pattern can have fewer than L literals, the patterns' maximum length is unconstrained and limited only by the size of the database.

Setting L to small values permits the identification of shorter conserved motifs that may be present in the processed input. As mentioned above, even if L is set to small values, patterns that are longer than L will be discovered and reported. Generally speaking, in order for a short motif to be considered statistically significant it will need to have a large number of copies in the processed input. Setting L to large values will generally permit the identification of statistically significant motifs even if these motifs repeat only a small number of times. This increase in specificity will happen at the expense of a potentially significant decrease in sensitivity.

For our work, L=4 was selected. This choice is dictated by the desire to capture potential commonalities among the seed regions of diverse microRNAs. Setting L to a value that is smaller than the 6 nucleotides typically associated with the seed regions gives us added flexibility. We also set W=12, a choice that is dictated by the desire to capture sequence commonalities where the local conservation is at least 33%. In other words, any reported pattern will have at most ⅔ of its positions occupied by wild cards. Finally, we set K=2. This is a natural consequence of the fact that we generate conserved sequence motifs through an unsupervised pattern discovery scheme. The value of 2 is the smallest possible one (a pattern or motif, by definition, must appear at least two times in the processed input) and guarantees that all patterns will be discovered.

Step 114 is the step of generating the reverse complement of patterns. For each of the patterns that were discovered in Step 112, we generate their reverse complement. For example, a typical mature microRNA pattern looks like:

```
                                              (SEQ ID NO: 2)
    [AT][CG].TTTTT[CG]G..[AT][AT][AT]G[CG].CTT
``` whereas its reverse complement will be

```
                                              (SEQ ID NO: 3)
    AAG.[CG]C[AT][AT][AT]..C[CG]AAAAA[CG][AT].
```

We next describe step 120, the identification of target sites. Step 120 is comprised of step 122, step 123 and step 124, as shown in FIG. 1.

Step 122 is the step of statistically filtering the patterns that were generated by step 114. Statistical filtering of the patterns that were generated by step 114 is done by estimating the log-probability of each pattern with the assistance of a Markov-chain. We next describe in detail how to use Markov chains to estimate the log-probabilities of patterns. The computation is carried out in the same manner for all of the patterns.

Real genomic data was used to estimate the frequency of trinucleotides that could span as many as 23 positions—there are at most 20 wild cards between the first and last nucleotide of the triplet. In other words, we computed the frequencies of all trinucleotides of the form:

```
    AAA
    AA.A
    AA..A
    ...
    AA...................A
    A.AA
    A.A.A
    A.A..A
    ...
    T....................TT
```

With these counts at hand, we used Bayes' theorem to estimate the probability that a given pattern could be generated from a random database. Let us use the pattern: A..[AT]. C..T...G to describe the approach. Observe that we can write:

Pr(A..[AT].C..T...G) =

Pr(C..T...G/A..[AT].C..T) =

Pr(C..T...G/C..T) * Pr(A..[AT].C..T) =

Pr(C..T...G/C..T) * Pr([AT].C..T/A..[AT].C) =

Pr(C..T...G/C..T) * Pr([AT].C..T/[AT].C) * Pr(A..[AT].C) =

Pr(C..T...G/C..T) * Pr([AT].C..T/[AT].C) * Pr(A..[AT].C/A..[AT]) =

(C..T...G)/(#(C..T...A) + #(C..T...C) + (C..T...G) + #(C..T...T)) *

([AT].C..T)/(#([AT].C..A) + #([AT].C..C) + #([AT].C..G) + #([AT]9.C..T)) *

(A..[AT].C)/(#(A..[AT].A) + #(A..[AT].C) + #(A..[AT].G) + #(A..[AT].T))

Note that all of the counts #(.) are available directly from the Markov chain and thus can be substituted for in the last equation. This in turn allows us to estimate the Pr(A..[AT]. C..T...G) (SEQ ID NO: 6) as well as the log(Pr(A..[AT]. C..T...G)) (SEQ ID NO: 7).

The present invention allows us to identify microRNA target sites independently of the knowledge of any given microRNA. The idea is as follows. It is known that mature microRNAs are first incorporated in the RNA-induced silencing complex (RISC) and subsequently bind to 3'UTR target sites through hybridization of complementary base pairs. Since our collection of patterns captures conserved, not necessarily contiguous sequence elements of mature microRNAs, it follows that the reverse complement of such patterns will permit us to locate conserved sequence elements in the untranslated regions of genes and, by consequence, putative microRNA-binding sites. These putative sites will correspond to 'hot spots' where a lot of patterns will aggregate. A typical mature microRNA pattern looks like

[AT][CG].TTTTT[CG]G..[AT][AT][AT]G[CG].CTT (SEQ ID NO: 8)

whereas its reverse complement will be

AAG.[CG]C[AT][AT][AT]..C[CG]AAAAA[CG][AT] (SEQ ID NO: 9).

In step 122, we applied statistical filtering on the patterns that were generated by step 114. In step 123, we use the 233,554 patterns that survived the statistical filtering of step 122 to locate the instances of the patterns in the 3'UTR of a gene of interest. An instance of the reverse complement of a mature microRNA pattern generates a "pattern hit" which covers as many nucleotides as the span of the corresponding pattern. This is repeated for all patterns. Clearly, a given nucleotide position within a 3'UTR may be hit by more than one pattern. This observation is used to associate 3'UTR regions which receive multiple pattern hits with putative microRNA target sites. Conversely, regions which do not correspond to target sites are expected to receive a much smaller number of hits, if any, which of course permits us to differentiate between background and microRNA target sites.

We demonstrate the validity of our key-idea with the help of the cog-1 gene from *C. elegans*: cog-1 is the target of microRNA cel-lsy-6. This is an important example because cel-lsy-6 is not contained in the January 2004 instance of the RFAM release from which we derived our pattern collection. Moreover, cel-lsy-6 has no significant sequence similarities with any of the microRNAs contained in that release, something that we established by using cel-lsy-6 as the query and running BLASTN to search the RFAM release in question.

Figure 2:
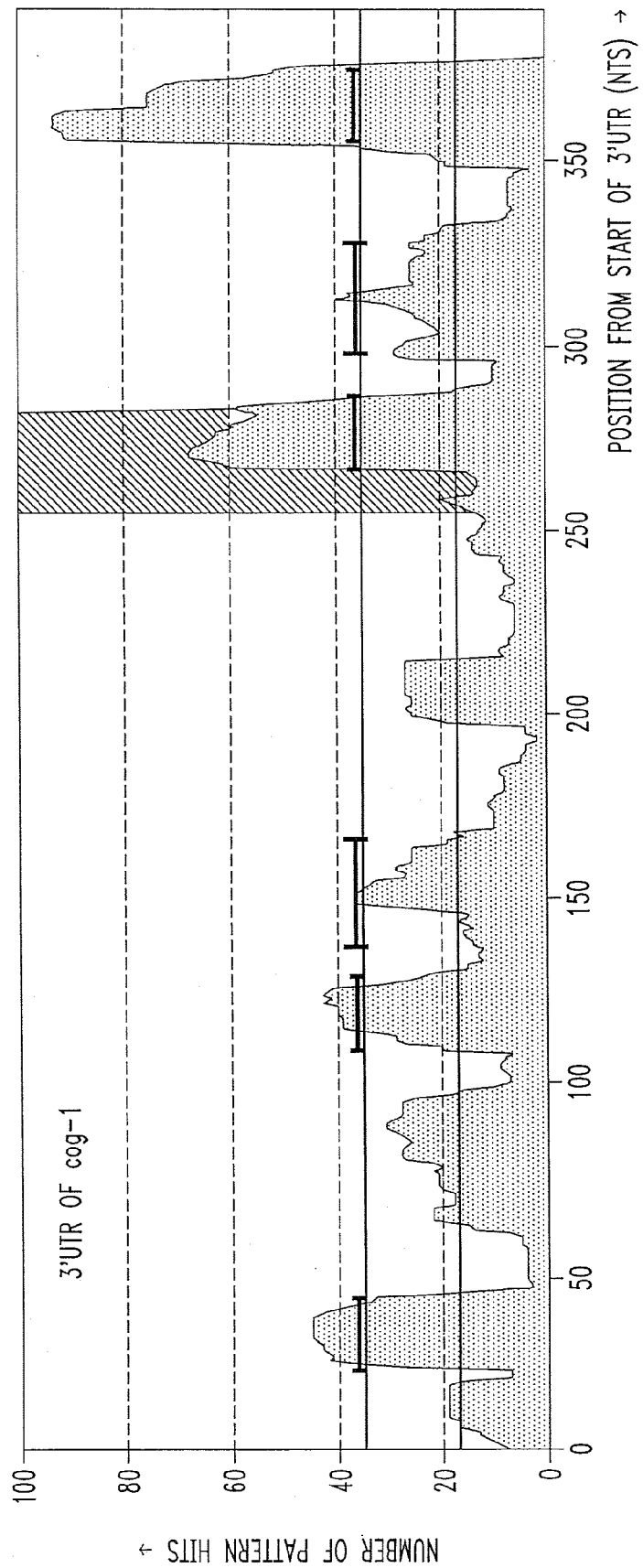
FIG. 2 is a graph illustrating the predicted and known microRNA binding sites within the 3'UTR of the cog-1 gene from C. elegans.

As shown in FIG. 2, processing cog-1's 3'UTR with the reverse complements of our microRNA patterns results in an accumulation of hits which is characterized by alternating peaks (regions hit by numerous patterns) and valleys (regions with low numbers of hits). By imposing a threshold of 35 pattern hits, we treat any locations with support below this level as 'background' and those which exceed it as sites where microRNAs will bind. The determination of the particular threshold level is discussed below.

FIG. 2 illustrates the predicted and known microRNA binding sites within the 3'UTR of the cog-1 gene from *C. elegans*. The histogram shows the number of pattern hits within the 3'UTR of cog-1. The solid, horizontal line at an offset of 35 shows the pattern hit threshold utilized by the method while the shaded rectangle highlights the experimentally proven binding site for lsy-6. The six black, horizontal segments shown are either 22 or 36 nucleotides in length.

One of the cog-1 regions exceeding threshold indeed coincides with the reported target site for cel-lsy-6—this site is shown in yellow in FIG. 2. The cel-lsy-6 binding site notwithstanding, five more regions exceed our pattern hit threshold in cog-1's 3'UTR. Of these regions, the rightmost one is, in fact, known to be the target site for a microRNA sequence, but the identity of this microRNA is not currently known. Notably, two of the regions exceeding threshold are substantially shorter than 22 nucleotides. In such cases, the inventive approach will report a 36-nucleotide-long interval, symmetrically placed around the region that exceeds threshold, as the predicted target site. Taken together, these findings lead us to hypothesize that cog-1 is under the control of additional (currently unidentified) microRNA sequences.

For the 233,554 patterns that we derived from the processed mature microRNA sequences, we sought the instances of the patterns in the 3'UTRs and 5'UTRs of every gene within ENSEMBL (Release 31) (Stabenau, A. et al. The ENSEMBL Core Software Libraries. *Genome Res.* 14 929-933 (2004)). An instance of a pattern contributes a vote of "+1" to all the UTR locations that the instance spans. This process can also be carried out in a similar manner using the sequences from the amino acid coding regions of the gene(s) instead of the sequences of the 3'UTRs and 5'UTRs.

Step 124 is the step of identifying "target islands" supported by a minimum number of pattern hits. All sequence regions comprising contiguous blocks of locations that were hit by $\geq 35$ patterns were kept and reported as "target islands." These target islands are putative microRNA binding sites. For regions shorter than 22 nucleotides in length, we report a 36-nucleotide segment that is centered on the original region and has appropriately-sized flanking segments surrounding the nucleotide segment.

Given the manner by which we determine pattern hits within the 3'UTR of a gene, it is clear that the extent of a region which receives support from multiple pattern hits will generally not be restricted to 22 nucleotides. It is possible that the span of contiguous locations that receive hits and are above threshold will be longer than 22 nucleotides. Given the statistically-significant character of the used patterns, it follows that all such blocks of contiguous locations which are supported by large numbers of pattern hits ought to be treated as distinct from background. In order to acknowledge the possibility that the length of these blocks can be larger than 22 nucleotides, we use the more permissive term target "island" instead of target "site." The underlying implication here is that those target islands whose lengths exceed 22 nucleotides correspond to multiple, juxtaposed or possibly overlapping microRNA target sites.

By identifying target islands in a UTR of interest we effectively focus the attention of the algorithm to only regions that receive support by the reverse complement of many mature microRNA patterns. This is a key pre-filtering step that discards all segments that are not deemed to be microRNA targets. As shown in the noise analysis below, and the experimental results corroborate, the target-island finding step is the key behind the observed resilience of the inventive approach.

We next describe step 130, the step of associating microRNA sequences with target islands. Step 130 is comprised of step 132 and step 134, as shown in FIG. 1.

Step 132 is the step of pairing-up each target island with each candidate microRNA sequence.

After having used the patterns to sub-select those 3'UTR segments on which to focus, we used the linker sequence GCGGGGACGC (SEQ ID NO: 10) (Stark, A. Brennecke, J. Russell, R. B. Cohen, S. M. Identification of Drosophila MicroRNA targets. *PloS Biol.* 1 397-409 (2003)) to pair each microRNA with every one of the target islands at all possible offsets.

Step 134 is the step of identifying and reporting microRNA/target-island partners whose interaction exceeds a predetermined threshold. Each resulting hybrid sequence took the form "mature microRNA-linker-predicted target island" and was processed by the Vienna package software, which allowed us to predict the hybrid's secondary RNA structure (Hofacker, I. L. et al. Fast Folding and Comparison of RNA Secondary Structures. *Monatsh. Chem.* 125 167-188 (1994)). Instead of the Vienna package, we could have used the 'mfold' algorithm to predict the hybrid's secondary RNA structure (Matthews, D. H., Sabina, J., Zuker, M. and Turner, D. H. Expanded Sequence Dependence of Thermodynamic Parameters Improves Prediction of RNA Secondary Structure. *J. Mol. Biol.* 288, 911-940 (1999)). Automated inspection of the predicted structure allows us to evaluate whether it conforms to a stem-loop-stem architecture, determine the locations (if any) where it self-hybridizes, and measure the quality and extent of base pairing between the microRNA sequence and the target island.

The Vienna package also reports the Gibbs free energy for the predicted structure ("folding energy"). Any structures that do not adhere to a strict 'stem-loop-stem' architecture are discarded. Also discarded are any structures which are predicted to self-hybridize at some location, even if the involved positions represent a negligible fraction of the total length of the complex. Finally, any structures with folding energy greater than −25 Kcal/mol, a very stringent threshold, are discarded. Note that the used linker contributes approximately −7 Kcal/mol to the total energy of the microRNA/mRNA complex. Also, more permissive energy thresholds can be used here (e.g. −18 Kcal/mol instead of −25 Kcal/mol) in order to improve the sensitivity of the inventive approach. All surviving structures are then ranked in an order that favors low folding energy, large numbers of matching base pairs, the presence of symmetrical arrangement of any predicted bulges, and minimal numbers of predicted G:U pairs among base pairs in the 'seed-region' of the microRNA.

Identification of the target islands forces the hybridization step to focus on and consider these sequence segments alone while ignoring the rest of the sequence. The target-island finding step is the key behind the performance of the inventive approach. Also, since each target island is examined in turn with each microRNA, the inventive approach will identify and report microRNA/target pairs involving juxtaposed or overlapping binding sites as long as each site is targeted by different microRNA sequences.

Unlike many of the previously reported target detection methods, the present invention does not need to enforce the 'seed-region' constraint in order to sub-select among potential target sites for a given microRNA sequence. These sites are decided during the target-islands finding step. This leads into increased flexibility and improved sensitivity when seeking targets of a microRNA sequence. As shown below, the existence of a seed-region signature in conjunction with extended base pairing and an energetically-favorable complex is not sufficient to guarantee repression of the target gene. This was true for predicted binding sites for all three microRNAs with which we experimented.

Lastly, as shown in step 139 of FIG. 1, the results (e.g., selected microRNA/target island interactions) of the above processes can be evaluated through experiment.

We will next describe the testing of the predictions using a standard luciferase reporter assay.

The computationally-predicted microRNA binding site sequence (~20-30 nucleotides), or microRNA-response-element (MRE), was synthesized as sense and antisense oligomers, annealed and cloned into psiCHECK-2 directly 3'-downstream of *Renilla* Luciferase (MRE-RLuc). 293T cells were seeded 24 hours before transfection at a density of $5 \times 10^4$ cells/well in 96-well plates. In the target validation of miR-375 & miR-296, 120 ng of over-expression vector or empty vector were cotransfected with 2 ng of the MRE-RLuc reporter vector using Lipofectamine 2000. In the target validation of miR-134, 12.5 nM of miR-134 mM or Scr oligo were cotransfected with 2 ng of the MRE-RLuc vector. Concurrently, additional controls were also performed using unpredicted MRE-RLuc (eg. antisense to miR-21) versus cognate microRNA or predicted MRE-RLuc versus non-cognate microRNAs (e.g. mmu-miR-21). In all cases, a constitutively expressed Firefly luciferase gene activity in psiCHECK-2 served as a normalisation control for transfection efficiency. 48-hours post-transfection, Firefly and *Renilla* luciferase activities were measured consecutively with the Dual-Luciferase® Reporter system by a luminometer. All luciferase assays were repeated a minimum of three times with 4 culture replicates each.

HEK 293T/17 (ATCC: CRL-11268) cells were cultured in Dulbecco's modified Eagle's medium. Appendixed with 10% heat-inactivated fetal bovine serum and penicillin/streptomycin, maintained at 37° C. with 5% $CO_2$.

Pre-miR™ microRNA precursor (134 mM) and the scrambled (Scr) RNA oligomer (AGACUAGCGGUAUCU-UUAUCCC) (SEQ ID NO: 11) were purchased from Ambion®.

To generate the over-expression vector for mmu-miR-375, a 500 bp (base pair) fragment was amplified by PCR from mouse genomic DNA using the Expand High Fidelity system and inserted into a modified pIRES-EGFP vector (EcoRI and BamHI sites). To generate the mmu-miR-296 and mmu-miR-21 over-expression vector, 500 bp fragments were amplified by PCR from mouse genomic DNA using the Expand High Fidelity system and inserted into the pLL3.7 lentiviral vector (Xho I & Hpa I sites).

A non-paired t-test was used to determine the significance of transfected cells relative to control transfected cells.

As mentioned above, we trained the inventive approach using an instance of the RFAM database which is more than 18 months old. Thus any microRNA/mRNA complexes that appeared in the literature after January 2004, and which are predicted correctly by the method should be considered to be valid, de novo predictions.

To date, only a relatively small number of microRNA target predictions have been supported experimentally in animals and they come from a handful of species (FIG. 3). To evaluate the ability of our inventive approach to correctly predict microRNA targets, we tested performance of the inventive approach on all (to the best of our knowledge) experimentally-supported microRNA binding sites which have been published to date. None of the previously-reported computational methods were evaluated for their ability to correctly predict the very diverse collection of microRNA/mRNA complexes studied herein. These results are summarized in FIG. 3. The cells with grey, vertical bars (respectively black-colored) cells of FIG. 3 (Part A) indicate that the method has correctly identified (respectively missed) the corresponding target site. For correctly identified (respectively missed) sites, the number of patterns hitting the target site is above (respectively below) threshold. Dark grey, dotted cells indicate that the inventive approach has discovered the known site partially. Also shown is the number of target islands at stated threshold. In Part (B) of FIG. 3, cells with grey, vertical bars (respectively black cells) show that the correct microRNA sequence was (respectively not) predicted by the inventive approach to hybridize with the known site. N/A: stands for "not applicable". We have selected the value 35 as our pattern-threshold.

In FIG. 3, the impact of various thresholds of pattern-support on the results of the inventive approach is shown. We report results for the interval [20,70] of values in increments of 5 pattern-hits. As can be seen, at a threshold of 20, the method succeeds in discovering all but 4 of the previously reported microRNA binding sites. Those of the reported sites which are outside the 3'UTRs currently listed in ENSEMBL have not been considered in this analysis (i.e., grey cells).

In addition to correctly identifying known microRNA target islands, the inventive approach is able to identify additional target islands in the 3'UTRs of the processed genes (clearly, the number of such predictions depends on the used threshold). For the examined threshold values, and for all of the processed 3'UTRs, the total number of target islands predicted by the method is listed in the FIG. 3. It is evident that the 3' UTRs for several of these genes contain numerous predicted target islands which persist even at very high thresholds (=support$\geq$60). As it is highly improbable that 60 or more of the used patterns (each of which is statistically significant in its own right) will coalesce to contribute hits to a block of contiguous locations simply by accident, we are led to hypothesize that these predicted target islands are likely valid (cf. the results shown in FIG. 2 for the 3'UTR of cog-1).

We decided on the pattern threshold to use in our analysis by studying the entries of FIG. 3. Even though a lower threshold would improve sensitivity, we decided to be conservative, and selected a value of 35 pattern-hits as our threshold. Using this threshold choice, the inventive approach correctly predicts 23 of the 31, or 74% of the reported sites that are contained within known 3'UTRs.

Further, it is examined how well the inventive approach can predict the microRNA sequence that will bind to those target sites which have already been correctly identified. The results are shown in FIG. 3. For almost every case where the inventive approach determined the correct binding site, it was able to also identify the correct microRNA sequence that targeted the site, and in full agreement with what has been reported in the literature. Enforcing the very stringent energy threshold of −25 Kcal/mol will result in the inventive approach missing three of the correct predictions namely lsy-6|cog-1, miR-375|mtpn and miR-141|clock (the corresponding ΔG values for the three missed pairs are shown in FIG. 3).

The reason for the stringent threshold choices stems from the desire to be conservative in our predictions. To this end, throughout the rest of the study, we will employ the thresholds for pattern hit, folding energy and minimum number of formed base pairs of 35, −25 Kcal/mol and 14 respectively.

A luciferase-reporter-based assay was chosen to test predicted targets sites. Each predicted microRNA binding site was inserted as a single copy directly downstream of a *Renilla* luciferase open reading frame (ORF). The use of tests where a single target site is examined each time formed an important component of the stringent strategy. Any reduction in luciferase activity could be attributed to a single source, thus showing that the putative target site is functional. The relative luciferase activity of the control transfection (scrambled RNA oligo or empty plasmid vector; represented as 100%) was compared to the activity when the cognate microRNA sequence was added. A sequence antisense to the targeting microRNA was used as a positive control whereas a sequence antisense to mmu-miR-21 was selected as a negative control (FIG. 4).

Figure 4A:
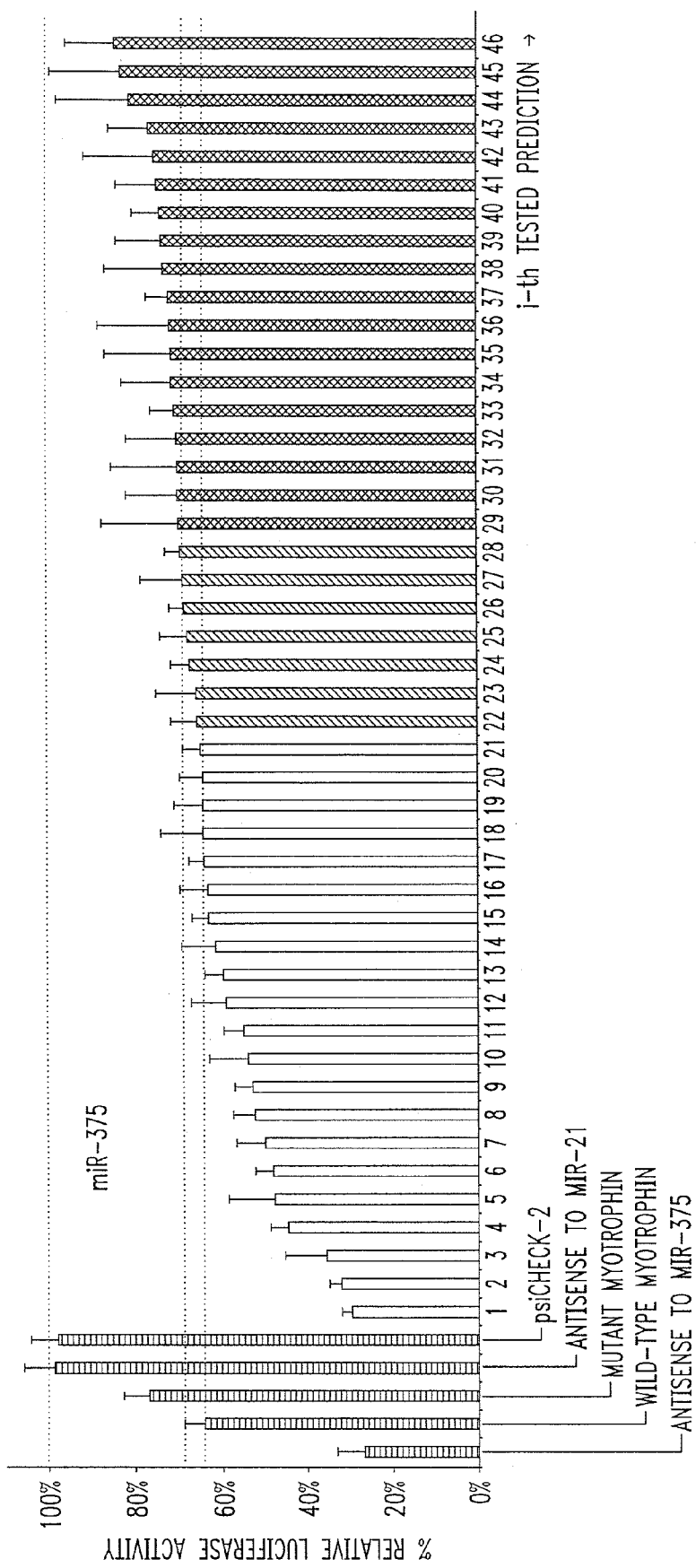
FIG. 4A is a graph illustrating luciferase-reporter assay results for the tested targets of miR-375.
Figure 4B:
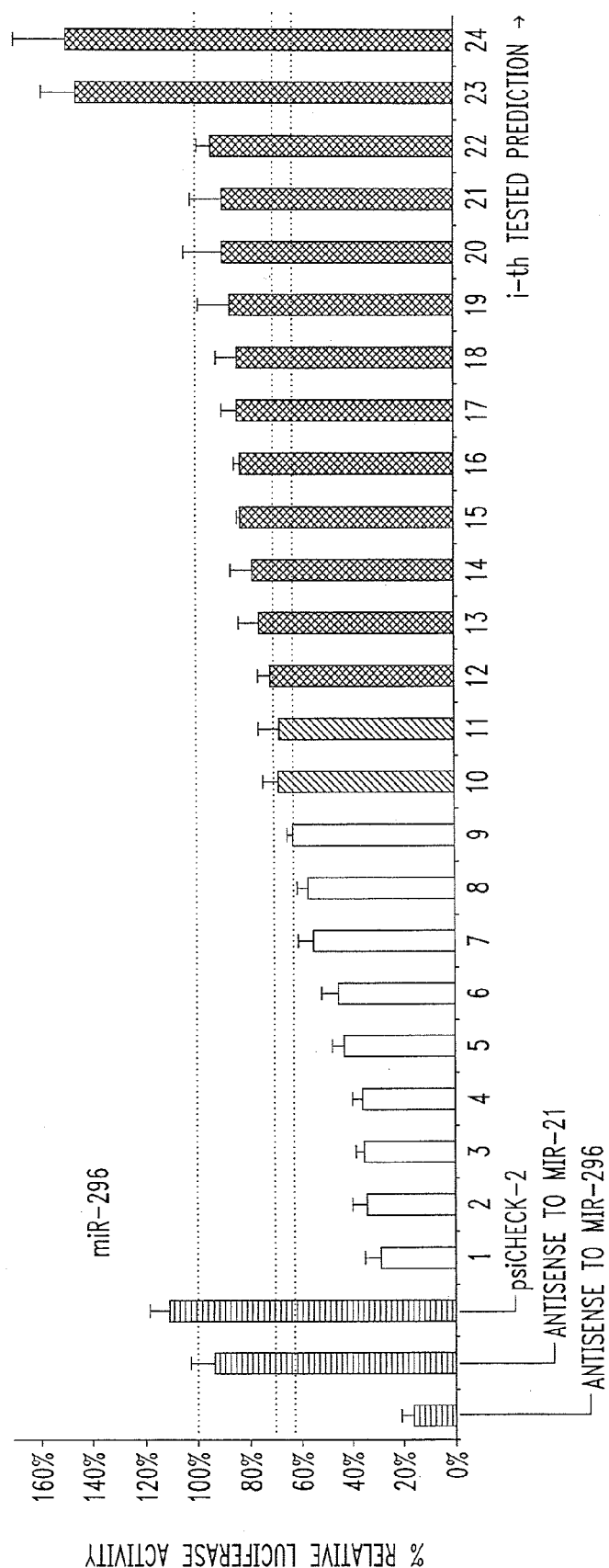
FIG. 4B is a graph illustrating luciferase-reporter assay results for the tested targets of miR-296.
Figure 4C:
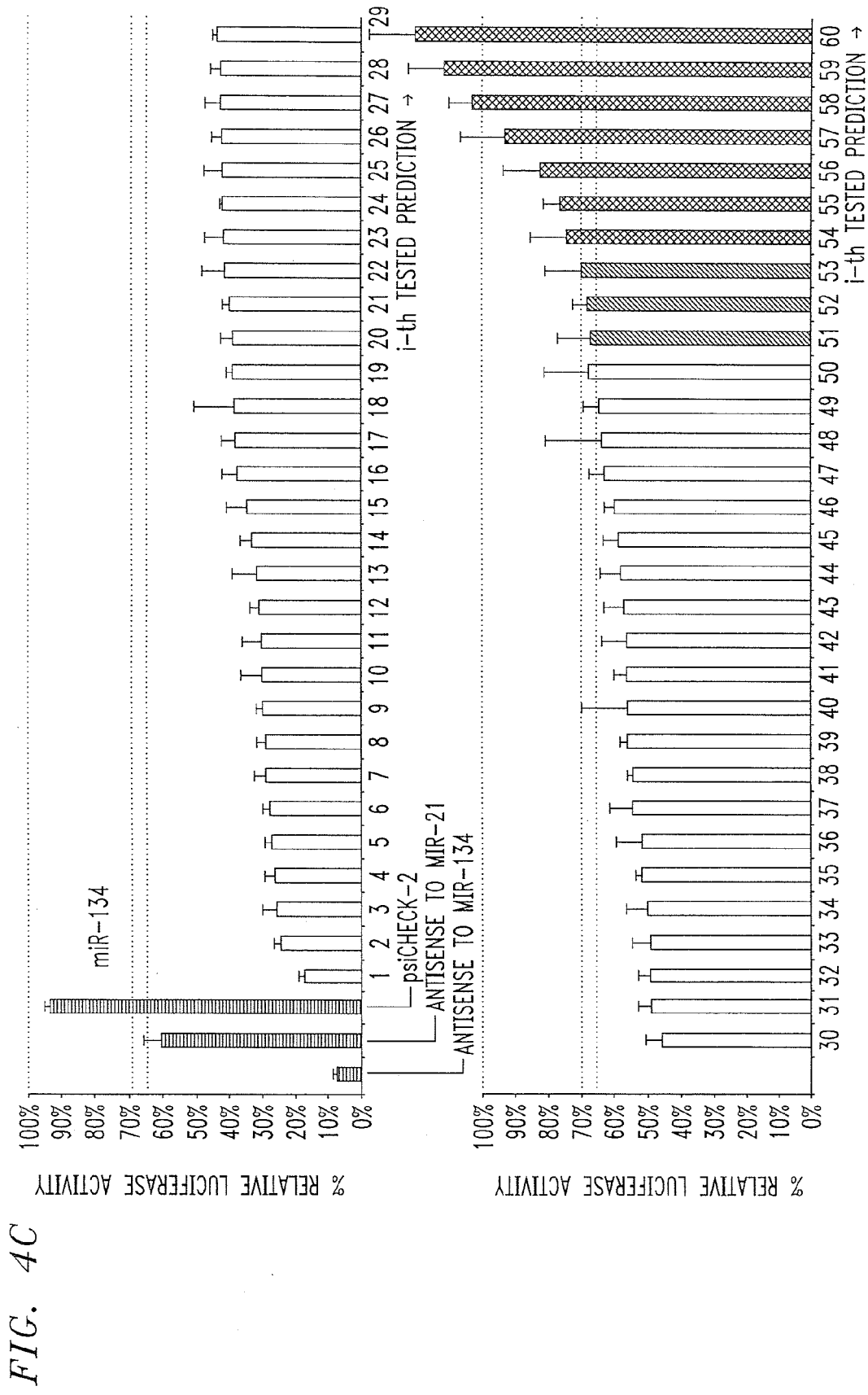
FIG. 4C is a graph illustrating luciferase-reporter assay results for the tested targets of miR-134.

FIG. 4A-C illustrates the luciferase-based validation of predicted targets in 293T cells. 293T cells were co-transfected with microRNA response element (MRE)+luciferase constructs and cognate microRNA (expression vector or synthetic RNA oligo) or control (empty vector or Scrambled RNA oligo; represented as 100%), where luciferase activity was measured 48-hours post-transfection and normalised to internal Firefly luciferase activity. Additional negative controls were also performed of all predicted MRE-luciferase reporters with non-cognate mmu-miR-21 (data not shown). In all the plots, the y-axis shows the relative level of luciferase expression, whereas the x-axis corresponds to the various experiments. The ENSEMBL identifiers of each studied target and the corresponding target sequence are listed herein. The luciferase activity which we measured for the wild-type myotrophin in the presence of miR-375 is used as the threshold throughout ($p<0.05$). Antisense to miR-134, miR-375, miR-296, miR-21 (100% complement to microRNAs). Luciferase vector without MRE is shown as psiCHECK-2. (Error bars, SE; n=12). FIG. 4A illustrates the luciferase-reporter assay results for the tested targets of miR-375. MRE sequence for wildtype & mutant myotrophin as adapted from Poy et al. FIG. 4B illustrates the luciferase-reporter assay results for the tested targets of miR-296. FIG. 4C illustrates the luciferase-reporter assay results for the tested targets of miR-134.

Additional negative controls were also done with other non-cognate microRNA sequences, as well as unrelated microRNA binding sites (data not shown). All luciferase-reporter assays were repeated a minimum of 3 times with 4 culture-replicates each. The assay demonstrated a ~30% reduction in wild-type myotrophin-luciferase activity in the presence of mmu-miR-375 thus providing further validation for the appropriateness of our setup.

For the experimental study, we considered three mouse microRNA sequences, namely mmu-miR-375, mmu-miR-134 and mmu-miR-296. MiR-375 was selected because its human homologue was recently characterized and shown to regulate insulin secretion by binding to myotrophin. The two other microRNAs, miR-134 and miR-296, were selected because they are significantly up-regulated during embryonic stem (ES) cell differentiation induced by retinoic acid (RA). Subsequent functional studies of miR-134 and miR-296 by over-expression or antisense inhibition demonstrated that they can modulate ES pluripotency markers (Oct4, Nanog, Utf-1) as well as various differentiation markers (Nestin, FGF-5). Moreover, modulation of ES differentiation mediated by mmu-miR-134 can be further enhanced by a combinatorial action with RA or embryoid body formation. Cellular assays also demonstrated that miR-134 and miR-296 over-expression can perturb the undifferentiated state of the mouse ES. In all three of the examples, we sought to computationally determine one or more of the targeted genes and experimentally verify them.

For the thresholds established above, and for each of miR-375, miR-134 and miR-296, the inventive approach predicted 2292, 2318 and 271 microRNA/mRNA complexes respectively. We prioritized among the predicted complexes using a ranking scheme that favored those with few/no mismatches and as few G:U pairs as possible in the seed region, complexes that contained small or no bulges and complexes with large numbers of matched base pairs. For the experimental analysis, we selected biochemically interesting predictions from the top-ranked positions in these three target collections. 46 predictions were selected for miR-375, 24 predictions for miR-296, and 60 from among the top 90 predictions for miR-134.

For a combined 79 of the 130 predictions that we tested we can show significant reduction in luciferase activity, well below the imposed threshold. For an additional 13 of the tested predictions, the observed reduction in luciferase activity was only slightly worse than the threshold. In FIG. 4 we show these results for miR-375, miR-296 and miR-134. The ENSEMBL identifiers and target site sequences for all 130 of the tested predictions are given above. Therein, we also show that RNAhybrid (Rehmsmeier, M. Steffen, P. Hochsmann, M. Giegerich, R. Fast and effective prediction of microRNA/target duplexes. *RNA* 10 1507-1517 (2004)) was able to report 51 and MiRanda (Enright, A. J. et al. MicroRNA targets in *Drosophila*. *Genome Biol.* 5 R1 (2003)) 50, out of a total of 79 validated binding sites, as the most likely candidates in the corresponding 3'UTRs.

The rank of each of the tested targets according to the luciferase assay and the rank each of the tested targets was assigned by the computational ranking scheme were found to be uncorrelated. This lack of correlation is important as it indicates that the ability of a microRNA sequence to repress a target is based on much more than the sequence-based rules that the computational ranking scheme incorporates. In fact, biological effectiveness against a particular target may be dependent on environment (e.g. mRNA localization), and the presence of machinery to target the gene (e.g. RNA binding proteins), such that differential effects of microRNAs on genes may be cell-type specific.

Consequently, the prioritization that we enforced on the predicted targets is tantamount to an arbitrary sub-selection from the original set of candidates. In other words, the tested target pairs represent a small arbitrary sample from the original pool of candidates. Consequently, the percentage of success that we observed in our experiments can be used to deduce that an analogous percentage of the original collection of predicted targets might be repressed by the microRNA sequence at hand.

Additional comments can be made based on the results of our luciferase assays. For example, for miR-375, we demonstrate that in addition to myotrophin several more targets may be repressed by this microRNA, and at levels greater than earlier reported. Notably, validated target #3 is from the 3'UTR of Kv2, a member of the voltage-dependent K+ channel family that is known to regulate insulin secretion. This raises the possibility that, in mice, miR-375 may modulate insulin secretion in additional ways but more experimental work will be necessary before this possibility can be established.

Arguably, most striking among the three sets of results are those obtained for miR-134, where 88% of the tested targets (53 out of the 60 we tested) show significant levels of repression. To further support our luciferase-reporter results, we assessed by immunoblots the level of protein production for 6 of miR-134's targets and were able to show that transfection of ES cells with miR-134 resulted in the decrease of protein product for 4 of the examined targets.

The 79 binding sites that were tested and validated were the unique, top-most prediction made by the inventive approach for the corresponding microRNA and 3'UTR combination. To study the impact of random inputs on the performance of the inventive approach, RNAhybrid and MiRanda, we created shuffled instances for the 79 3'UTRs that contained the validated target site of the inventive approach and presented them as input to all three algorithms.

Since these shuffled sequences are random strings, one expects that no algorithm should be reporting any binding sites for the three microRNA sequences at hand. Using default settings for all three algorithms, we found that RNAhybrid reported 706 microRNA/mRNA complexes on these random inputs and MiRanda reported 1,112 whereas the inventive approach reported only 5. The exceptional resilience of the inventive approach to noise is related to the target-island-finding step. The patterns used to discover target-islands are not expected to form aggregates exceeding threshold when applied to random strings of nucleotides. Consequently, very few, if any, target-islands will be available for the last step where we attempt to hybridize a microRNA sequence with a target-island. On the other hand, methods that use the dynamic programming approach to the local suffix alignment problem will generate numerous candidate complexes even on random strings.

Having demonstrated the method's predictive capability, we proceeded to process and analyze the 3'UTRs from the genomes of C. elegans, D. melanogaster, M. musculus and H. sapiens. The findings are summarized in FIG. 5A. As can be seen, between 74% and 92% of each organism's transcripts have one or more target islands identified in their 3'UTRs. With respect to the total number of 3'UTR locations which are predicted to participate in target islands, the number is again high. In fact, the percentage of the total number of 3'UTR nucleotides participating in predicted microRNA target sites ranges between 41% and 48% in the four studied genomes. It is worth noting that the currently known microRNAs form favorable (i.e. above our stringent thresholds) microRNA/mRNA complexes with many of the transcripts from these four genomes (see last column of FIG. 5A).

In view of recent work that raised the possibility for the existence of microRNA target sites in the 5'UTRs of transcripts, we used the inventive process to also process the available 5'UTRs of the four studied genomes. The results are shown in FIG. 5B. Between 31% and 53% of the transcripts have one or more target islands identified in their 5'UTRs. And the fraction of 5'UTR nucleotides that comprise predicted microRNA target sites ranges between 23% and 39%, i.e. it is substantially lower than in the 3'UTR case. There is a similar conjecture that microRNA target sites do exist in amino acid coding regions as well. Identifying such putative sites entails the use of the inventive process together with such sequences. We have already done so, but the results from the analysis escape the scope of the current presentation.

FIG. 5A is a table summarizing the results from the analysis of 3'UTRs of the microRNA target site predictions for the genomes of C. elegans, D. melanogaster, M. musculus and H. sapiens using the inventive approach. FIG. 5B is a table summarizing the results from the analysis of 5'UTRs of the microRNA target site predictions for the genomes of C. elegans, D. melanogaster, M. musculus and H. sapiens using the inventive approach.

FIGS. 6A-B is a table further summarizing of the microRNA target site predictions of the inventive approach for the genomes of C. elegans, D. melanogaster, M. musculus and H. sapiens. Specifically, FIG. 6A illustrates the average number of transcripts that a known microRNA sequence is predicted to target, and the average number of known microRNA sequences that are predicted to hit a transcript, assuming that the targeting takes place through the 3'UTR of the transcripts. FIG. 6B illustrates the average number of transcripts that a known microRNA sequence is predicted to target, and the average number of known microRNA sequences that are predicted to hit a transcript, assuming that the targeting takes place through the 5'UTR of the transcripts.

In FIG. 6, and for each of the four genomes we studied, we list the average number of transcripts that will be targeted by one of the known microRNAs from the corresponding genome, according to the inventive approach. Interestingly, the computational predictions for the genome of D. melanogaster are in agreement with those that were reported recently. Also shown is the average number of microRNA sequences that the inventive approach predicts will target each of the currently known transcripts for the genomes we studied. FIG. 6A shows the results for 3'UTRs and FIG. 6B shows the results for 5'UTRs.

FIG. 7 is a block diagram of a system 700 for determining whether a nucleotide sequence contains a microRNA binding site and which microRNA sequence will bind thereto in accordance with one embodiment of the present invention. System 700 comprises a computer system 710 that interacts with a media 750. Computer system 710 comprises a processor 720, a network interface 725, a memory 730, a media interface 735 and an optional display 740. Network interface 725 allows computer system 710 to connect to a network, while media interface 735 allows computer system 710 to interact with media 750, such as Digital Versatile Disk (DVD) or a hard drive.

As is known in the art, the methods and apparatus discussed herein may be distributed as an article of manufacture that itself comprises a computer-readable medium having computer-readable code means embodied thereon. The computer-readable program code means is operable, in conjunction with a computer system such as computer system 710, to carry out all or some of the steps to perform the methods or create the apparatuses discussed herein. The computer-readable code is configured to generate patterns processing a collection of already known mature microRNA sequences; assign one or more attributes to the generated patterns; subselect only the patterns whose attributes satisfy certain criteria; generate the reverse complement of the subselected patterns; and use the reverse complement of the subselected patterns to analyze the nucleotide sequence. The computer-readable medium may be a recordable medium (e.g., floppy disks, hard drive, optical disks such as a DVD, or memory cards) or may be a transmission medium (e.g., a network comprising fiber-optics, the world-wide web, cables, or a wireless channel using time-division multiple access, codedivision multiple access, or other radio-frequency channel). Any medium known or developed that can store information suitable for use with a computer system may be used. The computer-readable code means is any mechanism for allowing a computer to read instructions and data, such as magnetic variations on a magnetic medium or height variations on the surface of a compact disk.

Memory 730 configures the processor 720 to implement the methods, steps, and functions disclosed herein. The memory 730 could be distributed or local and the processor 720 could be distributed or singular. The memory 730 could be implemented as an electrical, magnetic or optical memory, or any combination of these or other types of storage devices. Moreover, the term "memory" should be construed broadly enough to encompass any information able to read from or written to an address in the addressable space accessed by processor 720. With this definition, information on a network, accessible through network interface 725, is still within memory 730 because the processor 720 can retrieve the information from the network. It should be noted that each distributed processor that makes up processor 720 generally contains its own addressable memory space. It should also be noted that some or all of computer system 710 can be incorporated into an application-specific or general-use integrated circuit.

Optional video display 740 is any type of video display suitable for interacting with a human user of system 700. Generally, video display 740 is a computer monitor or other similar video display.

It is to be appreciated that, in an alternative embodiment, the invention may be implemented in a network-based implementation, such as, for example, the Internet. The network could alternatively be a private network and/or local network. It is to be understood that the server may include more than one computer system. That is, one or more of the elements of FIG. 7 may reside on and be executed by their own computer system, e.g., with its own processor and memory. In an alternative configuration, the methodologies of the invention may be performed on a personal computer and output data transmitted directly to a receiving module, such as another personal computer, via a network without any server intervention. The output data can also be transferred without a network. For example, the output data can be transferred by simply downloading the data onto, e.g., a floppy disk, and uploading the data on a receiving module.

The present invention teaches a novel and robust pattern-based methodology for the identification of microRNA targets and their corresponding microRNA/mRNA complexes. With the help of patterns derived by processing the sequences of known mature microRNA sequences, the inventive approach identifies microRNA target islands within the 3'UTRs of transcripts. Then, inventive approach uses the information about these target islands to determine the identity of the targeting microRNA sequence.

The following are examples of advantages that characterize the inventive approach provided herein: a) the inventive approach obviates the need to enforce a cross-species conservation filtering before reporting results, thus allowing the discovery of microRNA targets that may not be shared even by closely related species; b) the inventive approach can be applied to the analysis of any genome that potentially harbors endogenous microRNAs without the need to be retrained each time; c) the inventive approach is able to identify target sites without having to know the identity of the targeting microRNA. This is a very important characteristic as the inventive approach permits the identification of target sites even if the targeting microRNA is not among those that have been identified to date.

The inventive approach can discover a large percentage of the currently validated target sites in the *C. elegans, D. melanogaster, M. musculus* and *H. sapiens* genomes. To the best of our knowledge, this is the first time that a microRNA target prediction algorithm has been subjected to such an extensive, demanding test. Moreover, we were able to achieve these results using a training set that by now is more than 18 months old.

Through additional experimentation with luciferase-reporter assays, where each predicted target site was inserted as a single copy directly downstream of the luciferase open reading frame, we validated a combined total of 79 predicted target sites for three mouse microRNA sequences, miR-375, miR-296 and miR-134. Of the 79 validated predictions of the inventive approach, only 51 and 50 respectively were also the top predictions made by RNAhybrid and MiRanda. Also, when presented with randomly shuffled instances of the complete 3'UTRs for the 79 validated targets the inventive approach exhibited exceptional resilience to noise far surpassing RNAhybrid and MiRanda.

We analyzed the 3'UTRs from the genomes of *C. elegans, D. melanogaster, M. musculus* and *H. sapiens* and found that a very large percentage of the transcripts of these genomes contain one or more microRNA binding sites. This result suggests the distinct possibility that microRNAs exert control on a much larger set of genes than originally believed. Consequently, it is entirely likely that microRNA target sites do exist in 5'UTRs and perhaps in the coding region of genes as well. Our preliminary analysis shows the existence of numerous target islands in the 5'UTRs (FIG. 5) and the coding regions (data not shown).

Notably, the present invention is the first method that can identify microRNA target sites without having to know the identity of the targeting microRNA. This implies that the inventive approach has the ability to discover sites targeted by microRNA sequences that are not contained in the currently available microRNA collections. Estimates resulting from the inventive approach analysis of genomic sequences suggest a much higher number of microRNA target sites. This bodes well with the recent discovery of previously-unreported human microRNA sequences, and our own contribution from applying the inventive approach to the discovery of microRNA precursors, which indicate that the number of endogenously-encoded microRNAs is likely to be much higher than originally hypothesized. As noted above, a method for identifying microRNA precursor sequences and corresponding mature microRNA sequences from genomic sequences is described in detail in the above-mentioned related U.S. patent application 11/351,951, the disclosure of which is incorporated herein.

With respect to the number of transcripts which are under microRNA control, the previous estimates were bound by the number of known mature microRNA sequences and were thus on the low side. Our computational analysis shows that for the four genomes we studied nearly all of their transcripts are targeted by microRNA sequences.

Although illustrative embodiments of the present invention have been described herein, it is to be understood that the invention is not limited to those precise embodiments, and that various other changes and modifications may be made by one skilled in the art without departing from the scope or spirit of the invention.

What is claimed is:

1. A method for determining whether a nucleotide sequence contains a microRNA binding site and which microRNA sequence will bind thereto, the method comprising the steps of:

generating one or more patterns by processing a collection of known mature microRNA sequences, wherein the one or more patterns comprise one or more intra- and inter-species patterns of conserved sequence segments, and wherein generating one or more patterns by processing a collection of known mature microRNA sequences is carried out by a component executing on a hardware processor;

generating a reverse complement of each generated pattern, wherein generating a reverse complement of each generated pattern is carried out by a component executing on a hardware processor;

assigning one or more attributes to the reverse complement of the one or more generated patterns, wherein assigning one or more attributes to the reverse complement of the one or more generated patterns is carried out by a component executing on a hardware processor;

subselecting the one or more patterns that correspond to a reverse complement having one or more assigned attributes that satisfy at least one criterion, wherein subselecting the one or more patterns is carried out by a component executing on a hardware processor, and wherein subselecting the one or more patterns comprises:

statistically filtering the one or more patterns by estimating a log-probability of each pattern, wherein statistically filtering the one or more patterns by estimating a log-probability of each pattern comprises:

using a Markov chain to estimate prior probabilities of multiple trinucleotide patterns spanning at most 23 positions and with, at most, 20 wild cards between the first and last nucleotide of each trinucleotide pattern; and using Bayes' theorem to calculate a posterior probability of each of the one or more patterns using the estimated prior probabilities of multiple trinucleotide patterns;

using the one or more patterns that survive the statistical filtering to locate one or more instances of the one or more surviving patterns in a 3'UTR of the nucleotide sequence; and identifying one or more target areas in the nucleotide sequence supported by a minimum number of pattern instances; and using each subselected pattern to analyze the nucleotide sequence, such that a determination is made whether the nucleotide sequence contains a microRNA binding site and which microRNA sequence will bind thereto, wherein using each subselected pattern to analyze the nucleotide sequence comprises pairing each of the one or more target areas with each of one or more candidate microRNA sequences, identifying one or more target area-microRNA pairs whose interaction exceeds a predetermined threshold and disregarding any pair with a folding energy greater than a predetermined threshold, and wherein using each subselected pattern to analyze the nucleotide sequence is carried out by a component executing on a hardware processor.

2. The method of claim 1, wherein the step of generating one or more patterns comprises using a pattern discovery algorithm.

3. The method of claim 1, wherein the step of assigning one or more attributes is carried out independently of and prior to the step of using the one or more patterns to analyze the nucleotide sequence.

4. The method of claim 1, wherein the one or more attributes are quantitative.

5. The method of claim 4, wherein at least one of the one or more attributes represents statistical significance.

6. The method of claim 4, wherein at least one of the one or more attributes represents a length of the pattern.

7. The method of claim 4, wherein the at least one of the one or more attributes represents a number of positions in the one or more patterns which are not occupied by wild cards.

8. The method of claim 1, wherein a threshold value for each attribute is selected.

9. The method of claim 8, wherein one or more patterns are discarded if the value of the one or more attributes of each pattern is below the selected threshold for the one or more attributes.

10. The method of claim 9, wherein the steps of selecting a threshold value and discarding one or more patterns are repeated for all used attributes.

11. The method of claim 1, wherein a set of counters is created for the nucleotide sequence.

12. The method of claim 11, wherein a number of counters in the set of counters equal the number of nucleotides in the nucleotide sequence.

13. The method of claim 11, wherein all patterns are examined to determine whether one or more patterns have an instance in the nucleotide sequence.

14. The method of claim 13, wherein each pattern with an instance in the nucleotide sequence contributes to the counters at the corresponding positions of the nucleotide sequence.

15. The method of claim 14, wherein only consecutive positions in the nucleotide sequences whose corresponding counter values exceed a threshold are considered.

16. The method of claim 15, wherein one or more groups of consecutive positions is reported if the one or more groups of consecutive positions satisfy a minimum length criterion.

17. The method of claim 16, wherein the one or more groups of consecutive positions are augmented by adding one or more flanking regions.

18. The method of claim 17, wherein the one or more augmented groups span at most 36 positions.

19. The method of claim 18, wherein the one or more augmented groups are reported.

20. The method of claim 19, wherein the one or more reported groups are examined together with one or more microRNA sequences.

21. The method of claim 20, wherein the one or more reported groups and the one or more microRNA sequence are hybridized into one or more complexes using one or more computational schemes.

22. The method of claim 21, wherein at least one of the one or more computational schemes is an RNA secondary structure prediction method.

23. The method of claim 22, wherein the prediction method is a method called 'mfold'.

24. The method of claim 21, wherein the one or more predicted complexes are assigned one or more attributes.

25. The method of claim 24, wherein at least one of the one or more attributes is free energy of the one or more formed complexes.

26. The method of claim 24, wherein at least one of the one or more attributes is a number of matching pairs in the one or more formed complexes.

27. The method of claim 24, wherein at least one of the one or more attributes is a number of bulges in the formed complex.

28. The method of claim 24, wherein a threshold value is selected for each attribute.

29. The method of claim 28, wherein one or more complexes are discarded if one or more attribute values does not exceed the selected threshold for the one or more attributes.

30. The method of claim 29, wherein the steps of selecting a threshold value and discarding one or more patterns are repeated for all used attributes.

31. The method of claim 30, wherein the nucleotide sequence and the one or more microRNA sequence forming the one or more complex are reported if the one or more complexes have not been discarded.

32. A system for determining whether a nucleotide sequence contains a microRNA binding site and which microRNA will bind thereto, comprising:

a memory that stores computer-readable code; and a processor operatively coupled to the memory, the processor configured to implement the computer-readable code, the computer-readable code configured to:

generate one or more patterns by processing a collection of known mature microRNA sequences, wherein the one or more patterns comprise one or more intra- and inter-species patterns of conserved sequence segments;

generate a reverse complement of each generated pattern;

assign one or more attributes to the reverse complement of the one or more generated patterns;

subselect the one or more patterns that correspond to a reverse complement having one or more assigned attributes that satisfy at least one criterion, wherein subselecting the one or more patterns comprises:

statistically filtering the one or more patterns by estimating a log-probability of each pattern, wherein statistically filtering the one or more patterns by estimating a log-probability of each pattern comprises:

using a Markov chain to estimate prior probabilities of multiple trinucleotide patterns spanning at most 23 positions and with, at most, 20 wild cards between the first and last nucleotide of each trinucleotide pattern; and using Bayes' theorem to calculate a posterior probability of each of the one or more patterns using the estimated prior probabilities of multiple trinucleotide patterns;

using the one or more patterns that survive the statistical filtering to locate one or more instances of the one or more surviving patterns in a 3'UTR of the nucleotide sequence; and identifying one or more target areas in the nucleotide sequence supported by a minimum number of pattern instances; and use each subselected pattern to analyze the nucleotide sequence, such that a determination is made whether the nucleotide sequence contains a microRNA binding site and which microRNA sequence will bind thereto, wherein using each subselected pattern to analyze the nucleotide sequence comprises pairing each of the one or more target areas with each of one or more candidate microRNA sequences, identifying one or more target area-microRNA pairs whose interaction exceeds a predetermined threshold and disregarding any pair with a folding energy greater than a predetermined threshold.

33. An article of manufacture for determining whether a nucleotide sequence contains a microRNA binding site and which microRNA will bind thereto, comprising:

a tangible computer readable recordable storage medium having computer-readable code embodied thereon, the computer-readable code comprising:

a step to generate one or more patterns by processing a collection of known mature microRNA sequences, wherein the one or more patterns comprise one or more intra- and inter-species patterns of conserved sequence segments;

a step to generate a reverse complement of each generated pattern;

a step to assign one or more attributes to the reverse complement of the one or more generated patterns;

a step to subselect the one or more patterns that correspond to a reverse complement having one or more assigned attributes that satisfy at least one criterion, wherein subselecting the one or more patterns comprises:

statistically filtering the one or more patterns by estimating a log-probability of each pattern, wherein statistically filtering the one or more patterns by estimating a log-probability of each pattern comprises:

using a Markov chain to estimate prior probabilities of multiple trinucleotide patterns spanning at most 23 positions and with, at most, 20 wild cards between the first and last nucleotide of each trinucleotide pattern; and using Bayes' theorem to calculate a posterior probability of each of the one or more patterns using the estimated prior probabilities of multiple trinucleotide patterns;

using the one or more patterns that survive the statistical filtering to locate one or more instances of the one or more surviving patterns in a 3'UTR of the nucleotide sequence; and identifying one or more target areas in the nucleotide sequence supported by a minimum number of pattern instances; and a step to use each subselected pattern to analyze the nucleotide sequence, such that a determination is made whether the nucleotide sequence contains a microRNA binding site and which microRNA sequence will bind thereto, wherein using each subselected pattern to analyze the nucleotide sequence comprises pairing each of the one or more target areas with each of one or more candidate microRNA sequences, identifying one or more target area-microRNA pairs whose interaction exceeds a predetermined threshold and disregarding any pair with a folding energy greater than a predetermined threshold.

* * * * *